US011389582B2

(12) United States Patent
Askem et al.

(10) Patent No.: US 11,389,582 B2
(45) Date of Patent: Jul. 19, 2022

(54) NEGATIVE PRESSURE WOUND THERAPY APPARATUS WITH REMOVABLE PANELS

(71) Applicant: T.J.Smith and Nephew, Limited, Hull (GB)

(72) Inventors: Ben Alan Askem, Leeds (GB); Ali Khishdoost Borazjani, Hull (GB); Nicola Brandolini, Beverley (GB); Matt Ekman, Hull (GB); Fatoona Mosa, Hull (GB); Felix Clarence Quintanar, Hull (GB); Hannah Bailey Sidebottom, Hull (GB)

(73) Assignee: T.J. Smith and Nephew, Limited, Hull (GB)

( * ) Notice: Subject to any disclaimer, the term of this patent is extended or adjusted under 35 U.S.C. 154(b) by 261 days.

(21) Appl. No.: 16/648,467

(22) PCT Filed: Sep. 24, 2018

(86) PCT No.: PCT/EP2018/075757
§ 371 (c)(1),
(2) Date: Mar. 18, 2020

(87) PCT Pub. No.: WO2019/063467
PCT Pub. Date: Apr. 4, 2019

(65) Prior Publication Data
US 2020/0230302 A1  Jul. 23, 2020

Related U.S. Application Data

(60) Provisional application No. 62/565,566, filed on Sep. 29, 2017.

(51) Int. Cl.
*A61M 27/00* (2006.01)
*A61M 1/00* (2006.01)
(Continued)

(52) U.S. Cl.
CPC ........... *A61M 1/90* (2021.05); *A61M 2205/15* (2013.01); *A61M 2205/18* (2013.01);
(Continued)

(58) Field of Classification Search
CPC ...... A61M 27/00; A61M 39/00; A61M 39/04; A61M 39/22; A61M 39/26; A61M 39/28;
(Continued)

(56) References Cited

U.S. PATENT DOCUMENTS

D239,019 S   3/1976 Flinn
4,498,850 A   2/1985 Perlov et al.
(Continued)

FOREIGN PATENT DOCUMENTS

CN       103357076      10/2013
DE   10 2015 215165 A1   2/2017
(Continued)

OTHER PUBLICATIONS

"Battery Charger", Wikipedia, accessed Nov. 9, 2018, in 12 pages. URL: https://web.archive.org/web/20181109005000/https://en.wikipedia.org/wiki/Battery_charger.
(Continued)

*Primary Examiner* — Tatyana Zalukaeva
*Assistant Examiner* — Ilya Y Treyger
(74) *Attorney, Agent, or Firm* — Knobbe, Martens, Olson & Bear, LLP

(57) ABSTRACT

Embodiments of negative pressure wound closure devices, systems and methods are disclosed. In some embodiments, a negative pressure apparatus includes a pump housing comprising a pump, a controller, and at least one light source and a panel removably attachable to the pump housing and configured to cover the at least one light source, the removable panel comprising one or more icons. The at least one light source can be configured to illuminate the one or more
(Continued)

icons when the removable panel is attached to the pump housing.

20 Claims, 17 Drawing Sheets

(51) Int. Cl.
  A61M 39/00 (2006.01)
  A61M 39/04 (2006.01)
  A61M 39/22 (2006.01)
  A61M 39/26 (2006.01)
  A61M 39/28 (2006.01)
  F04B 45/00 (2006.01)

(52) U.S. Cl.
  CPC .............. A61M 2205/3306 (2013.01); A61M 2205/3375 (2013.01); A61M 2205/3382 (2013.01); A61M 2205/52 (2013.01); A61M 2205/581 (2013.01); A61M 2205/582 (2013.01); A61M 2205/583 (2013.01); A61M 2205/587 (2013.01)

(58) Field of Classification Search
  CPC ... A61M 1/0023; A61M 2205/11; F04B 45/00
  See application file for complete search history.

(56) References Cited

U.S. PATENT DOCUMENTS

| | | |
|---|---|---|
| 4,731,076 A | 3/1988 | Noon et al. |
| D357,735 S | 4/1995 | McPhee |
| 5,514,088 A | 5/1996 | Zakko |
| 5,712,795 A | 1/1998 | Layman et al. |
| 6,027,490 A | 2/2000 | Radford et al. |
| 6,203,291 B1 | 3/2001 | Stemme et al. |
| 6,232,680 B1 | 5/2001 | Bae et al. |
| 6,396,407 B1 | 5/2002 | Kobayashi |
| D475,132 S | 5/2003 | Randolph |
| 7,004,915 B2 | 2/2006 | Boynton et al. |
| 7,022,113 B2 | 4/2006 | Lockwood et al. |
| 7,070,584 B2 | 7/2006 | Johnson et al. |
| 7,214,202 B1 | 5/2007 | Vogel et al. |
| D581,042 S | 11/2008 | Randolph et al. |
| D590,934 S | 4/2009 | Randolph et al. |
| D602,582 S | 10/2009 | Pidgeon et al. |
| D602,583 S | 10/2009 | Pidgeon et al. |
| D602,584 S | 10/2009 | Pidgeon et al. |
| 7,608,066 B2 | 10/2009 | Vogel |
| 7,611,500 B1 | 11/2009 | Lina et al. |
| D625,801 S | 10/2010 | Pidgeon et al. |
| 7,857,806 B2 | 12/2010 | Karpowicz et al. |
| D630,313 S | 1/2011 | Pidgeon et al. |
| D630,725 S | 1/2011 | Pidgeon et al. |
| 7,927,319 B2 | 4/2011 | Lawhorn |
| D645,137 S | 9/2011 | Gonzalez |
| 8,021,348 B2 | 9/2011 | Risk, Jr. et al. |
| 8,062,272 B2 | 11/2011 | Weston |
| 8,066,243 B2 | 11/2011 | Svedman et al. |
| 8,070,735 B2 | 12/2011 | Koch et al. |
| D654,164 S | 2/2012 | Cole et al. |
| D660,409 S | 5/2012 | Taggerty et al. |
| 8,215,929 B2 | 7/2012 | Shen et al. |
| 8,216,197 B2 | 7/2012 | Simmons et al. |
| 8,226,620 B2 | 7/2012 | Giezendanner et al. |
| 8,308,714 B2 | 11/2012 | Weston et al. |
| 8,317,774 B2 | 11/2012 | Adahan |
| 8,366,692 B2 | 2/2013 | Weston |
| 8,409,160 B2 | 4/2013 | Locke et al. |
| 8,480,641 B2 | 7/2013 | Jacobs |
| 8,540,688 B2 | 9/2013 | Eckstein et al. |
| 8,641,693 B2 | 2/2014 | Locke et al. |
| 8,668,677 B2 | 3/2014 | Eckstein et al. |
| 8,827,967 B2 | 9/2014 | Lawhorn |
| 8,858,517 B2 | 10/2014 | Pan et al. |
| 8,905,985 B2 | 12/2014 | Allen et al. |
| 9,050,398 B2 | 6/2015 | Armstrong et al. |
| 9,084,845 B2 | 7/2015 | Adie et al. |
| 9,138,531 B2 | 9/2015 | Yodfat et al. |
| 9,199,010 B2 | 12/2015 | Yao et al. |
| D750,222 S | 2/2016 | Chang |
| D750,235 S | 2/2016 | Maurice |
| D750,236 S | 2/2016 | Maurice |
| D757,260 S | 5/2016 | Lombardi, III et al. |
| 9,327,063 B2 | 5/2016 | Locke et al. |
| 9,333,281 B2 | 5/2016 | Giezendanner et al. |
| D764,047 S | 8/2016 | Bjelovuk et al. |
| D764,048 S | 8/2016 | Bjelovuk et al. |
| D764,653 S | 8/2016 | Bjelovuk et al. |
| D764,654 S | 8/2016 | Bjelovuk et al. |
| 9,415,199 B2 | 8/2016 | Tsai |
| 9,427,505 B2 | 8/2016 | Askem et al. |
| D765,830 S | 9/2016 | Bjelovuk et al. |
| 9,445,948 B2 | 9/2016 | Smola |
| D773,658 S | 12/2016 | Bow |
| 9,586,036 B2 | 3/2017 | Masuda et al. |
| D788,293 S | 5/2017 | Eckstein |
| 9,682,179 B2 | 6/2017 | May |
| D791,939 S | 7/2017 | Tuturro et al. |
| D792,586 S | 7/2017 | Becker |
| 9,737,649 B2 | 8/2017 | Begin et al. |
| D797,275 S | 9/2017 | Evans et al. |
| D802,744 S | 11/2017 | Bjelovuk et al. |
| 9,901,664 B2 | 2/2018 | Askem |
| D813,374 S | 3/2018 | Bjelovuk et al. |
| D814,016 S | 3/2018 | Bjelovuk et al. |
| D815,726 S | 4/2018 | Bjelovuk et al. |
| D815,727 S | 4/2018 | Bjelovuk et al. |
| D820,980 S | 6/2018 | Maurice |
| 9,923,401 B2 | 10/2018 | Jung |
| 10,124,093 B1 | 11/2018 | Francis et al. |
| 10,143,785 B2 | 12/2018 | Adams et al. |
| 10,155,070 B2 | 12/2018 | Childress et al. |
| D842,460 S | 3/2019 | Gierse et al. |
| D851,759 S | 6/2019 | Jones et al. |
| D852,356 S | 6/2019 | Steele et al. |
| 2002/0013545 A1 | 1/2002 | Soltanpour et al. |
| 2002/0030002 A1 | 3/2002 | Verkaart et al. |
| 2002/0098097 A1 | 7/2002 | Singh |
| 2004/0057855 A1 | 3/2004 | Gerlach et al. |
| 2004/0068224 A1 | 4/2004 | Couvillon, Jr. et al. |
| 2005/0234485 A1 | 10/2005 | Seegert et al. |
| 2006/0281398 A1 | 12/2006 | Yokomizo et al. |
| 2008/0031748 A1 | 2/2008 | Ihle et al. |
| 2009/0216205 A1 | 8/2009 | Ryan et al. |
| 2009/0299306 A1 | 12/2009 | Buan |
| 2010/0244780 A1 | 9/2010 | Turner |
| 2011/0006876 A1 | 1/2011 | Moberg et al. |
| 2011/0060300 A1 | 3/2011 | Weig et al. |
| 2011/0076170 A1 | 3/2011 | Fujisaki et al. |
| 2011/0196291 A1 | 8/2011 | Vischer et al. |
| 2012/0136325 A1* | 5/2012 | Allen ................... A61M 1/743 604/319 |
| 2012/0289913 A1 | 11/2012 | Eckstein et al. |
| 2013/0012772 A1 | 1/2013 | Gunday et al. |
| 2013/0025692 A1 | 1/2013 | Heide et al. |
| 2013/0237937 A1 | 9/2013 | Ramella et al. |
| 2013/0267917 A1 | 10/2013 | Pan et al. |
| 2013/0274718 A1 | 10/2013 | Yao et al. |
| 2013/0302545 A1 | 11/2013 | Schnelker et al. |
| 2014/0023533 A1 | 1/2014 | Ishii et al. |
| 2014/0276488 A1 | 9/2014 | Locke et al. |
| 2015/0174320 A1 | 6/2015 | Grant et al. |
| 2015/0231021 A1 | 8/2015 | Smith et al. |
| 2015/0246164 A1 | 9/2015 | Heaton et al. |
| 2015/0320916 A1 | 11/2015 | Croteau et al. |
| 2016/0015872 A1 | 1/2016 | Luckemeyer et al. |
| 2016/0015957 A1 | 1/2016 | Tieck et al. |
| 2016/0101278 A1 | 4/2016 | Norris et al. |
| 2016/0136339 A1 | 5/2016 | Begin et al. |
| 2016/0213843 A1 | 7/2016 | Despa et al. |
| 2016/0250398 A1 | 9/2016 | Barr et al. |
| 2016/0271305 A1 | 9/2016 | Kurihara et al. |

(56) References Cited

U.S. PATENT DOCUMENTS

| | | |
|---|---|---|
| 2016/0303358 A1 | 10/2016 | Croizat et al. |
| 2017/0165405 A1 | 6/2017 | Muser et al. |
| 2017/0189588 A1 | 7/2017 | Croizat et al. |
| 2017/0189666 A1 | 7/2017 | Sealfon et al. |
| 2017/0216501 A1 | 8/2017 | Armstrong et al. |
| 2017/0296716 A1 | 10/2017 | Middleton et al. |
| 2017/0319758 A1 | 11/2017 | Eddy et al. |
| 2017/0354767 A1 | 12/2017 | Carr et al. |
| 2018/0001000 A1 | 1/2018 | Herwig et al. |
| 2018/0021178 A1 | 1/2018 | Locke et al. |
| 2018/0104391 A1 | 4/2018 | Luxon et al. |
| 2018/0140466 A1 | 5/2018 | Hunt |
| 2018/0250459 A1 | 9/2018 | Kimball et al. |
| 2018/0318476 A1 | 11/2018 | Askem et al. |
| 2018/0326129 A1 | 11/2018 | Askem et al. |
| 2019/0167867 A1 | 6/2019 | Adams et al. |
| 2019/0192744 A1 | 6/2019 | Greener et al. |
| 2019/0358372 A1 | 11/2019 | Askem et al. |
| 2021/0077670 A1 | 3/2021 | Long et al. |

FOREIGN PATENT DOCUMENTS

| | | |
|---|---|---|
| EP | 1 955 887 | 8/2008 |
| EP | 3 124 059 | 2/2017 |
| EP | 3 124 060 | 2/2017 |
| FR | 2 939 320 | 6/2010 |
| GB | 1220857 | 1/1971 |
| JP | S56-047279 | 4/1981 |
| JP | H01-101978 | 4/1989 |
| JP | H07-96029 | 4/1995 |
| JP | 2007-218241 | 8/2007 |
| JP | 6047279 B2 | 12/2016 |
| WO | WO-9605873 A1 | 2/1996 |
| WO | WO 2000/061206 | 10/2000 |
| WO | WO 2003/081762 | 10/2003 |
| WO | WO 2004/077387 | 9/2004 |
| WO | WO 2008/033788 | 3/2008 |
| WO | WO 2008/039223 | 4/2008 |
| WO | WO-2009071924 A1 | 6/2009 |
| WO | WO 2011/075706 | 6/2011 |
| WO | WO-2011094410 A2 | 8/2011 |
| WO | WO 2012/004298 | 1/2012 |
| WO | WO 2012/100624 | 8/2012 |
| WO | WO 2013/015827 | 1/2013 |
| WO | WO-2013064852 A1 | 5/2013 |
| WO | WO-2013078214 A1 | 5/2013 |
| WO | WO 2014/115819 | 7/2014 |
| WO | WO 2014/164655 | 10/2014 |
| WO | WO 2015/197462 | 12/2015 |
| WO | WO 2016/018448 | 2/2016 |
| WO | WO 2016/109048 | 7/2016 |
| WO | WO 2017/ 027850 A1 * | 7/2016 |
| WO | WO 2017/027850 | 2/2017 |
| WO | WO 2017/044138 | 3/2017 |
| WO | WO 2017/062042 | 4/2017 |
| WO | WO 2017/160412 | 9/2017 |
| WO | WO 2017/197357 A1 | 11/2017 |
| WO | WO 2017/197357 A4 | 1/2018 |
| WO | WO 2018/009873 | 1/2018 |
| WO | WO 2018/009880 | 1/2018 |
| WO | WO 2018/041854 | 3/2018 |
| WO | WO 2018/150263 | 8/2018 |
| WO | WO 2018/150267 | 8/2018 |
| WO | WO 2018/150268 | 8/2018 |
| WO | WO 2018/167199 | 9/2018 |
| WO | WO-2018195101 A1 | 10/2018 |
| WO | WO 2019/063467 | 4/2019 |
| WO | WO 2019/129581 | 7/2019 |
| WO | WO 2019/179943 | 9/2019 |
| WO | WO 2019/211730 | 11/2019 |
| WO | WO 2019/211731 | 11/2019 |
| WO | WO 2019/211732 | 11/2019 |
| WO | WO 2019/224059 | 11/2019 |
| WO | WO 2020/011690 | 1/2020 |

OTHER PUBLICATIONS

International Search Report and Written Opinion, re PCT Application No. PCT/EP2018/075757, dated Jan. 14, 2019.

International Preliminary Report on Patentability, re PCT Application No. PCT/EP2018/075757, dated Apr. 9, 2020.

Jenkins R.W., et al., "Mechanisms of Resistance to Immune Checkpoint Inhibitors," British Journal of Cancer, Jan. 2, 2018, vol. 118, https://doi.org/10.1038/bjc.2017.434, pp. 9-16.

* cited by examiner

NEGATIVE PRESSURE WOUND THERAPY APPARATUS WITH REMOVABLE PANELS

CROSS-REFERENCE TO RELATED APPLICATIONS

This application is a U.S. national stage application of International Patent Application No. PCT/EP2018/075757, filed Sep. 24, 2018, which claims priority to U.S. Provisional Patent Application No. 62/565,566, filed on Sep. 29, 2017, the entire disclosure of which is incorporated by reference herein.

BACKGROUND

Field

Embodiments or arrangements disclosed herein relate to methods and apparatuses for dressing and treating a wound with topical negative pressure (TNP) therapy. For example, but without limitation, any embodiments disclosed herein may relate to treating a wound with reduced pressure. As another non-limiting example, any embodiments disclosed herein relate to apparatuses and methods for controlling the operation of a TNP system.

Description of Related Art

Many different types of wound dressings are known for aiding in the healing process of a human or animal. These different types of wound dressings include many different types of materials and layers, for example, pads such as gauze pads or foam pads. Topical negative pressure ("TNP") therapy, sometimes referred to as vacuum assisted closure, negative pressure wound therapy, or reduced pressure wound therapy, is widely recognized as a beneficial mechanism for improving the healing rate of a wound. Such therapy is applicable to a broad range of wounds such as incisional wounds, open wounds and abdominal wounds or the like.

TNP therapy assists in the closure and healing of wounds by reducing tissue edema; encouraging blood flow; stimulating the formation of granulation tissue; removing excess exudates, and may reduce bacterial load and thus reduce the potential for infection of the wound. Furthermore, TNP therapy permits less outside disturbance of the wound and promotes more rapid healing.

SUMMARY

Disclosed embodiments relate to negative pressure wound closure devices, methods, and systems that facilitate closure of a wound. It will be understood by one of skill in the art that the wounds described herein this specification may encompass any wound, and are not limited to a particular location or type of wound. The devices, methods, and systems may operate to reduce the need for repetitive replacement of wound dressing material currently employed and can advance the rate of healing. The devices, methods, and systems may be simultaneously used with negative pressure to remove wound fluids.

In certain embodiments, an apparatus for treating a wound with negative pressure wound therapy is provided, the apparatus comprises a pump housing and a panel removably attachable to the pump housing. The pump housing may have a pump, a controller, and at least one light source. The panel may cover at least one of the light sources. The panel can have one or more icons. The at least one light source may illuminate the one or more icons of the panel when the panel is attached to the pump housing.

The apparatus of the preceding paragraph can further include one or more of the following features. The at least one light source can illuminate the one or more icons in response to the controller detecting at least one of a plurality of conditions. The plurality of conditions can include at least one of a power on, low battery, leak, or canister full. The one or more icons can provide an indication to a user regarding the condition detected by the controller. The pump housing may permit a plurality of removable panels to be attached to the housing. The plurality of removable panels may each have a different arrangement of icons. The controller can determine which of the plurality of removable panels is attached to the pump unit and change one or more pump settings based on the determination. The plurality of icons may be printed on an inner surface of the removable panel.

In certain embodiments, an apparatus for treating a wound with negative pressure wound therapy is provided, the apparatus comprises a pump housing and one or more panels configured to be removably attachable to the pump housing. The pump housing can have a pump and a controller. The pump may provide, via a fluid flow path, negative pressure to a wound configured to be covered by a wound dressing. The one or more panels may indicate an operating mode. A first operating mode of the pump can be associated with a first panel. The controller can operate the pump in the first operating mode in response to detecting that the first panel is attached to the pump housing. The controller may adjust one or more operational parameters of the pump based on the first operating mode.

The apparatus of the preceding paragraph can further include one or more of the following features. The one or more operating modes may include a canister mode or a canisterless mode. The pump housing can further include a recess to receive the one or more panels. The pump housing can further include a switch. The one or more panels may each engage the switch to indicate whether a canister is positioned in the fluid flow path between the pump and the wound. The switch can include at least one of a capacitive sensor, an inductive sensor, an infrared sensor, an ultrasonic sensor, an optical sensor, or a photodetector. The one or more panels can each have a plurality of icons. The one or more panels can each have a different arrangement of icons. The pump housing can include a plurality of light sources to illuminate one or more of the plurality of icons. The plurality of light sources can illuminate the icons in response to the operating mode. The operating mode can be indicated by the first panel. The controller can operate the pump in a second operating mode in response to detecting that a second panel is attached to the pump housing. The second operating mode can be associated with the second panel and different from the first operating mode. The controller can adjust the one or more operational parameters of the pump based on the second operating mode. The pump housing can further include a detector in communication with the controller. At least some of the one or more panels may engage the detector configured to indicate to the controller whether a canister is positioned in the fluid flow path between the pump and the wound based on the output of the detector. The first panel of the one or more panels can be configured to indicate that the canister is positioned in the fluid flow path and is further configured to engage the detector when attached to the housing. A second panel of the one or more panels can be configured to indicate that the canister is not positioned in the fluid flow path and is further configured not to engage the detector when attached to the housing. The detector can include at least one of a capacitive sensor, an inductive sensor, an infrared sensor, an ultrasonic sensor, an optical sensor, a photodetector, or a mechanical switch.

In certain embodiments, a method for operating a wound with negative pressure wound therapy is provided, the method comprises: in response to a panel being removably connected to a housing comprising a negative pressure source, determining an operating parameter associated with the panel, based on the operating parameter, determining whether a canister or a wound dressing without a separate canister is fluidically connected to the negative pressure source, and adjusting provision of negative pressure from the negative pressure source based on the determination. The method is performed under control of a controller.

The method of the preceding paragraph can further include one or more of the following features. The method can further include determining which panel of a plurality of panels is removably connected to the housing. Each panel of the plurality of panels can be associated with a different operating parameter. The method can further include operating the negative pressure source in one or more modes in response to determining which panel is attached to the housing. The step of operating in the one or more modes can include adjusting one or more operational parameters of the negative pressure source based on the mode. The method can further include adjusting a user interface configured to provide at least one operational parameter of the apparatus based on the determination.

Other embodiments of wound closure devices, stabilizing structures and associated apparatuses are described below.

BRIEF DESCRIPTION OF THE DRAWINGS

Other features and advantages of the present disclosure will be apparent from the following detailed description, taken in conjunction with the accompanying drawings of which.

DETAILED DESCRIPTION

Overview

Embodiments disclosed in this section or elsewhere in this specification relate to apparatuses and methods of treating a wound with reduced pressure, including pump and wound dressing components and apparatuses. The apparatuses and components comprising the wound overlay and packing materials, if any, are sometimes collectively referred to in this section or elsewhere in this specification as dressings.

It will be appreciated that throughout this specification reference is made to a wound. It is to be understood that the term wound is to be broadly construed and encompasses open and closed wounds in which skin is torn, cut or punctured or where trauma causes a contusion, or any other superficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, abdominal wounds or other large or incisional wounds, either as a result of surgery, trauma, sterniotomies, fasciotomies, or other conditions, dehisced wounds, acute wounds, chronic wounds, subacute and dehisced wounds, traumatic wounds, flaps and skin grafts, lacerations, abrasions, contusions, burns, electrical burns, diabetic ulcers, pressure ulcers, stoma, surgical wounds, trauma and venous ulcers or the like.

Embodiments of the present disclosure are generally applicable to use in topical negative pressure (TNP) or reduced pressure therapy systems. Briefly, negative pressure wound therapy assists in the closure and healing of many forms of "hard to heal" wounds by reducing tissue edema, encouraging blood flow and granular tissue formation, or removing excess exudate and can reduce bacterial load (and thus infection risk). In addition, the therapy allows for less disturbance of a wound leading to more rapid healing. TNP therapy systems can also assist in the healing of surgically closed wounds by removing fluid. In some embodiments, TNP therapy helps to stabilize the tissue in the apposed position of closure. A further beneficial use of TNP therapy can be found in grafts and flaps where removal of excess fluid is important and close proximity of the graft to tissue is required in order to ensure tissue viability.

Negative Pressure System

Figure 1:
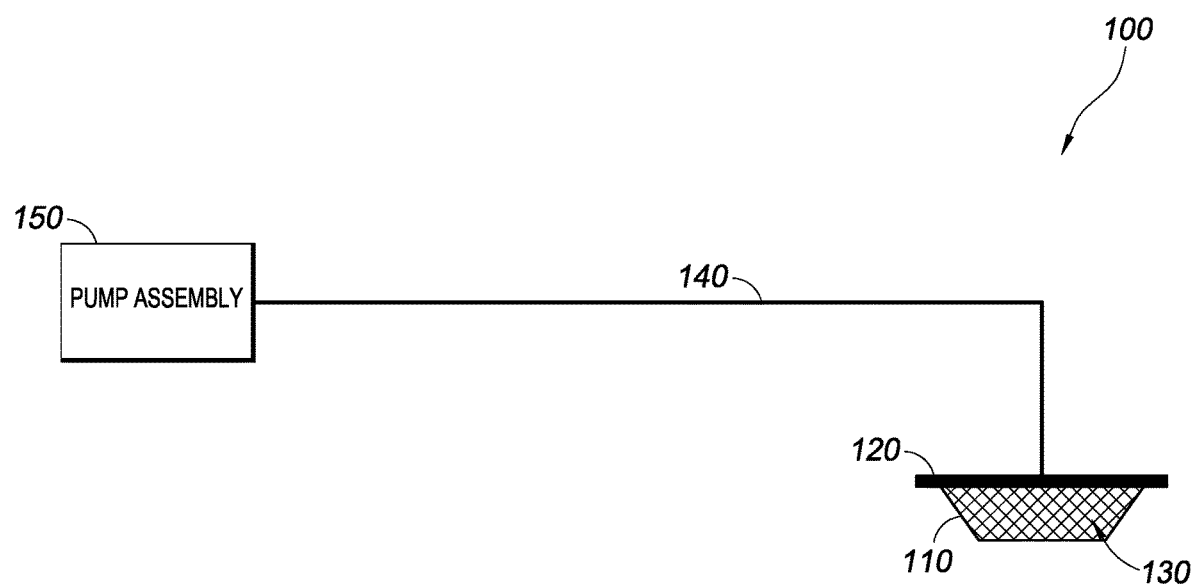
FIG. 1 illustrates a reduced pressure wound therapy system including a pump assembly according to some embodiments.

FIG. 1 illustrates a negative or reduced pressure wound treatment (or TNP) system 100 according to some embodiments. The system 100 comprises a wound filler 130 placed inside a wound cavity 110, the wound cavity 110 sealed by a wound cover 120. In some embodiments, one or more of the wound filler 130, the wound cover 120, or any other component, such as a contact layer (not shown), make up a wound dressing. The system 100 includes a negative pressure wound therapy apparatus or a pump assembly 150 configured to provide reduced pressure to the wound. For example, a conduit 140 having at least one lumen can provide a fluid flow path between the pump assembly 150 and the wound. The conduit 140 can have a pump end 142 that is fluidically connected to the pump assembly 150 and a wound end 144 that is inserted under or through the wound cover 120. The conduit 140 can communicate a negative pressure at the pump end 142 to the wound end 144.

Figure 2A:
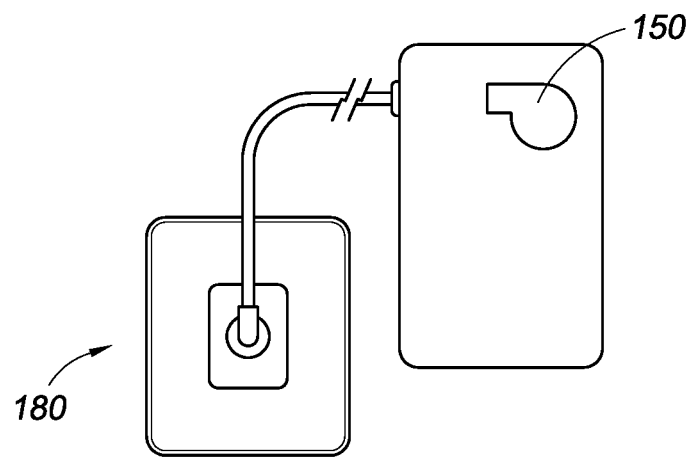
FIG. 2A illustrates a reduced pressure wound therapy system operating in a canisterless mode of operation according to some embodiments.
Figure 2B:
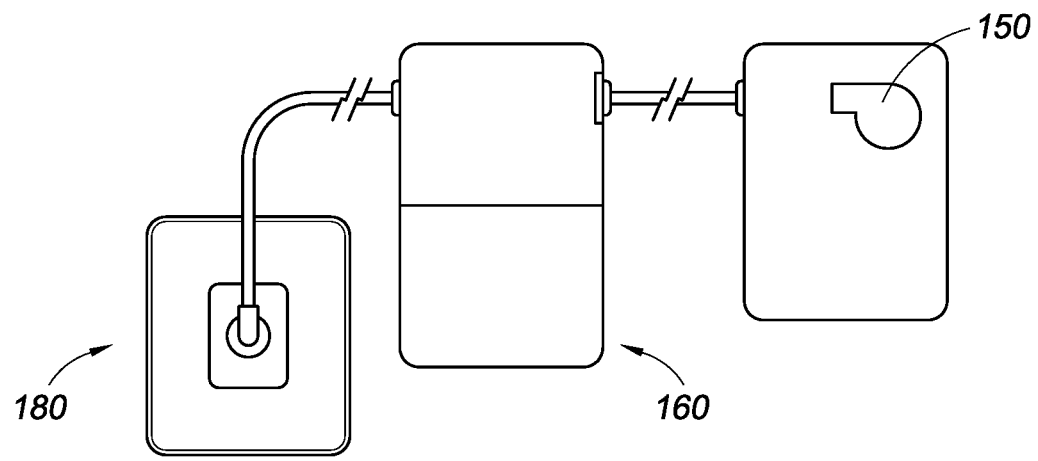
FIG. 2B illustrates a reduced pressure wound therapy system operating in a canister mode of operation according to some embodiments.

FIGS. 2A-2B illustrate that the reduced pressure wound therapy system can be configured to operate with and without a canister (for example, canister and canisterless modes) according to some embodiments. FIG. 2A shows an embodiment of the TNP system 100 that has a wound dressing 180 connected directly to the pump assembly 150 (for example, canisterless mode). FIG. 2B shows an embodiment of the TNP system 100 that has a canister 160 interposed between a wound dressing 180 and the pump assembly 150 (for example, canister mode). At the beginning of the application of negative pressure wound therapy to a wound when the wound is in the early stages of the healing process and exudes a significant volume of exudate, the reduced pressure wound therapy system may operate with a canister. In this mode of operation, the negative pressure wound therapy system may operate with a foam or gauze RENASYS™ dressing sold by Smith & Nephew or any other suitable dressing. Operation of the reduced pressure wound therapy system with a canister may sometimes be referred to herein as "RENASYS", "RENASYS-mode", or derivatives thereof. As the wound is progressing through the healing process and is starting to exude a smaller volume of exudate, the canister may be removed and the negative pressure wound therapy system may operate with an absorbent dressing, such as the PICO™ dressing sold by Smith & Nephew or any other suitable dressing that retains the wound exudate within the dressing. Operation of the reduced pressure wound therapy system without a canister may sometimes be referred to herein as "PICO", "PICO-mode", or derivatives thereof.

Pump Assembly

Figure 3A:
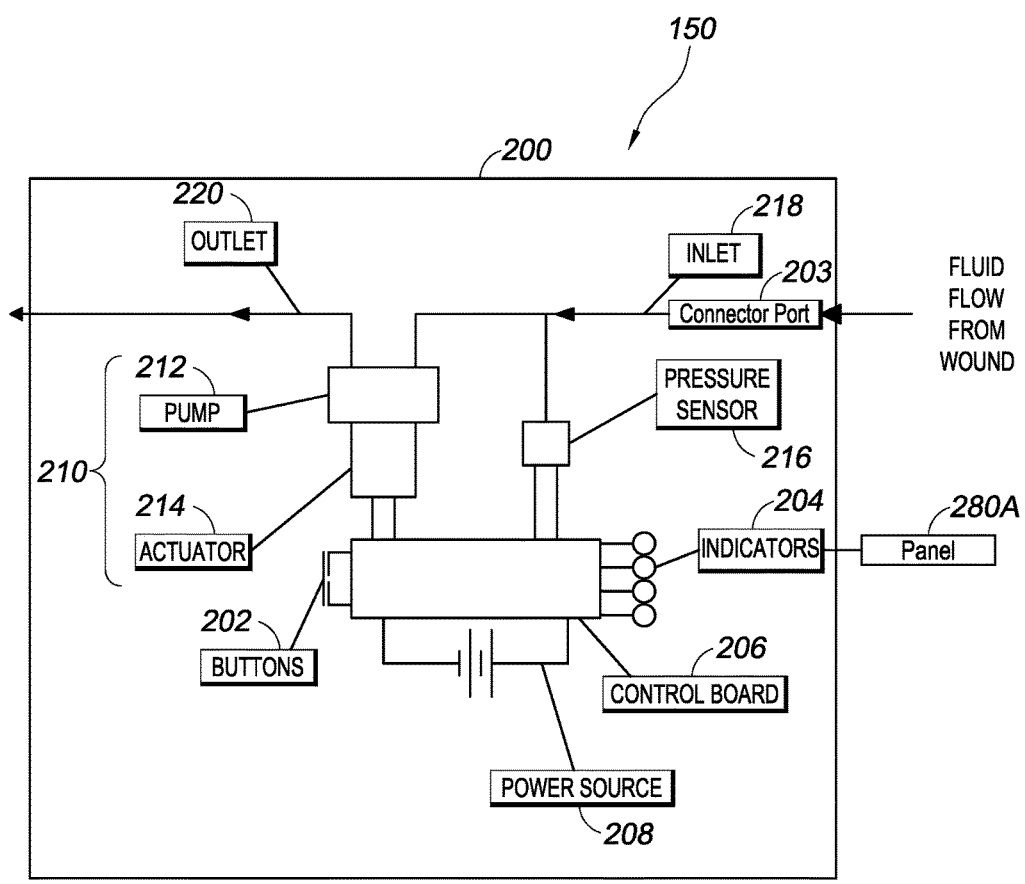
FIGS. 3A-3B illustrates a schematic of a reduced pressure wound therapy system including a pump assembly according to some embodiments.

FIG. 3A illustrates a schematic of the pump assembly 150 according to some embodiments. The pump assembly 150 can include a housing 200 that encloses or supports at least some components of the pump assembly 150. The pump assembly 150 can include one or more switches or buttons 202, one or more indicators 204, and a control board 206. The one or more buttons 202 and the one or more indicators 204 (which collectively make up a user interface) can be in electrical communication with the control board 206, which can include one or more controllers and memory. The one or more buttons 202 can be used for any suitable purpose for controlling an operation of the pump assembly 150. For example, the one or more buttons 202 can be used to activate the pump system 150, pause the pump assembly 150, and clear system indicators such as one or more of the one or more indications 204. The one or more buttons 202 can by any type of switch or button, such as a touchpad, touch screen, keyboard, and so on. In some embodiments, the one or more buttons 202 can be a press button. In various implementations, one or more buttons 202 can be included on a touchscreen interface.

Figure 3B:
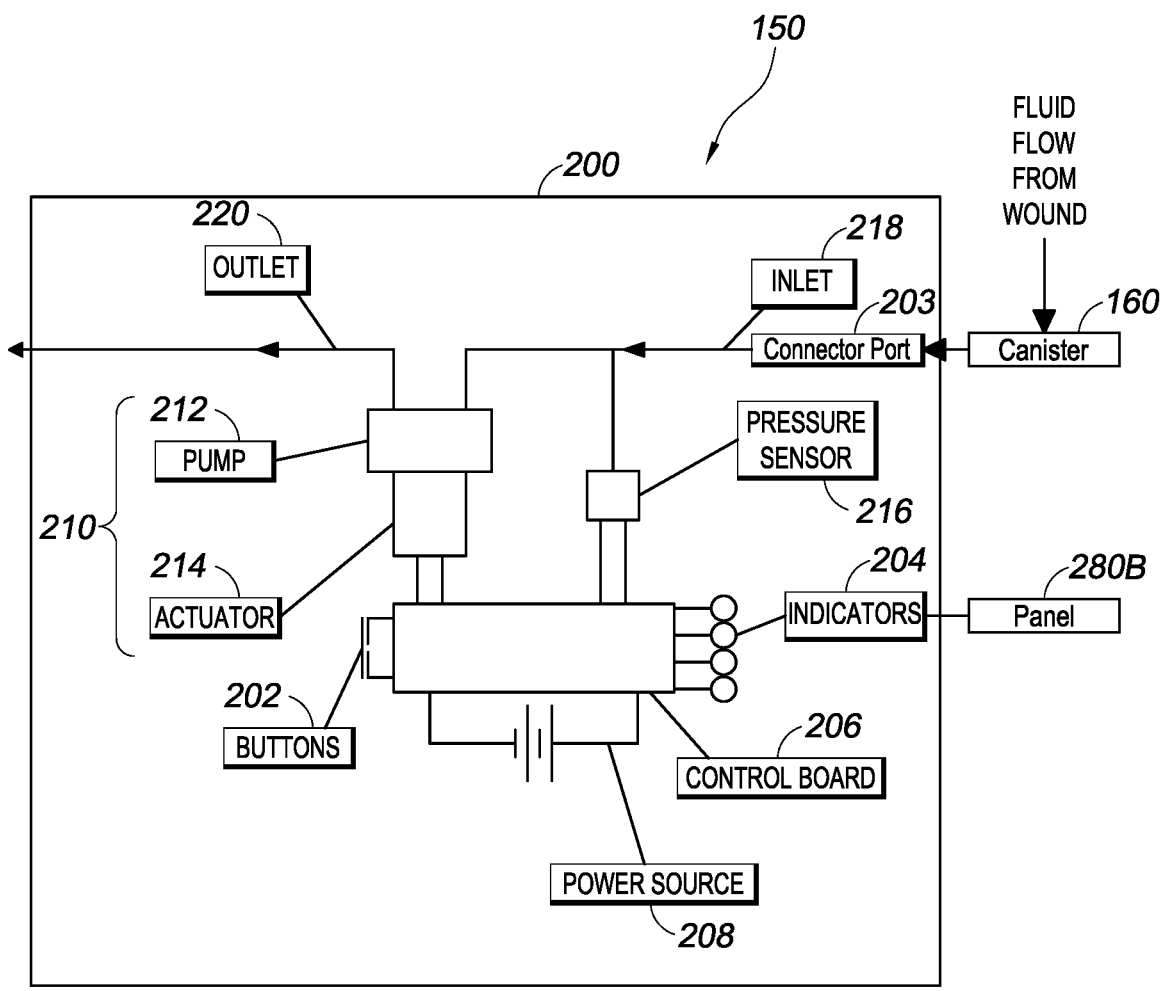

The pump assembly 150 can include one or more interchangeable interfaces, for example a panel 280, adapted to be removably attached to the housing 200. The panel 280 may be configured to indicate a mode of operation to the pump assembly 150. For example, the panel 280 may signal to the pump assembly to operate in one or more modes, such as canister mode and canisterless mode. In some instances, attaching a first panel 280A to the housing 200 may indicate to the pump assembly 150 to begin operating in canisterless mode (for example, as illustrated in FIG. 3A). The first panel 280A may be removed from the pump assembly 150 and replaced with a second panel 280B that is then attached to the pump assembly 150. The second panel 280B may indicate to the pump assembly 150 to operate in canister mode (for example, as illustrated in FIG. 3B). By way of another example, a second panel 280B that is configured to indicate that the pump assembly 150 is connected to a RENASYS™ dressing can be removed from the housing 200 and replaced with a first panel 280A that is configured to indicate a connection to a PICO™ dressing, thereby allowing the pump assembly 150 switch from a canister mode of operation to a canisterless mode of operation. As described herein, the panel 280 can be adapted to allow the pump assembly 150 to determine whether a canister is attached to the connector port 203. In some arrangements, the operation of the pump assembly 150 can be adjusted according to whether a panel 280 attached to the housing indicates that a canister is connected to the connector port 203.

In some embodiments, the control board 206 (for example, a controller) adjusts one or more operational parameters of negative pressure wound therapy depending on the operating mode of the pump assembly 150. For example, in canisterless mode, the level of negative pressure provided to the wound can be reduced compared to canister mode because the wound is exuding a smaller amount of fluid. As another example, detection of one or more operating conditions can be enabled, disabled, or adjusted. For instance, in canisterless mode, canister full detection (or blockage detection) and alarming can be disabled and, instead, dressing full detection and alarming can be enabled. As another example, user may be allowed to adjust the pressure set point in canister mode, but not in canisterless mode.

The pump assembly 150 can be powered by a power source 208 such as a battery power cell or any other suitable power source. The pump assembly 150 can also include a source of negative pressure 210, which can include a pump 212 powered by an actuator 214, such as an electric motor, a voice coil motor, a piezoelectric actuator, or the like. In some embodiments, the actuator 214 is integrated into the pump 212. The negative pressure source 210 can be a rotary diaphragm pump or other diaphragm pump, a piezoelectric pump, a peristaltic pump, a piston pump, a rotary vane pump, a liquid ring pump, a scroll pump, a diaphragm pump operated by a piezoelectric transducer, a pump operated by a voice coil actuator, or any other suitable pump or micropump or any combinations of the foregoing, The pump assembly 150 can also include one or more pressure sensors 216 that measure pressure in the fluid flow path.

The pump assembly 150 can further include an inlet 218 to connect the pump assembly 150 to the wound dressing. For example, the inlet 218 can be connected to the connector port 203 that is in fluid communication with the wound dressing via a fluid flow path.

The pump assembly 150 can also include an outlet 220. The outlet 220 can vent or exhaust gas to the atmosphere. In some embodiments, a filter (not shown) can be interposed between the outlet 220 and the atmosphere. The filter can provide filtration of the gas prior to venting the gas to the atmosphere. The filter can be a bacterial filter, odor filter, or any combination thereof. In some embodiments, a dampening component (not shown), such as a noise dampening component, can be interposed between the outlet 220 and the atmosphere. The dampening component can reduce the noise generated by the pump assembly 150 during operation. In some implementations, the pump assembly 150 can communicate information, such as information related to provision of negative pressure therapy, to one or more remote devices. Such communication can be performed using a wired or wireless interface.

FIG. 3B illustrates the pump assembly 150 of FIG. 3A with a canister 160 additionally positioned in a fluid flow path between the inlet 218 and the wound dressing. In the illustrated embodiment, the canister 160 fluidically connects to the connector port 203. As discussed in further detail herein, a panel 280 removably attached to the housing 200 can be configured to signal to the pump assembly 150 whether the connector port 203 is connected to a wound dressing directly or whether a canister 160 is disposed between the connector port 203 and the wound dressing.

Figure 4:
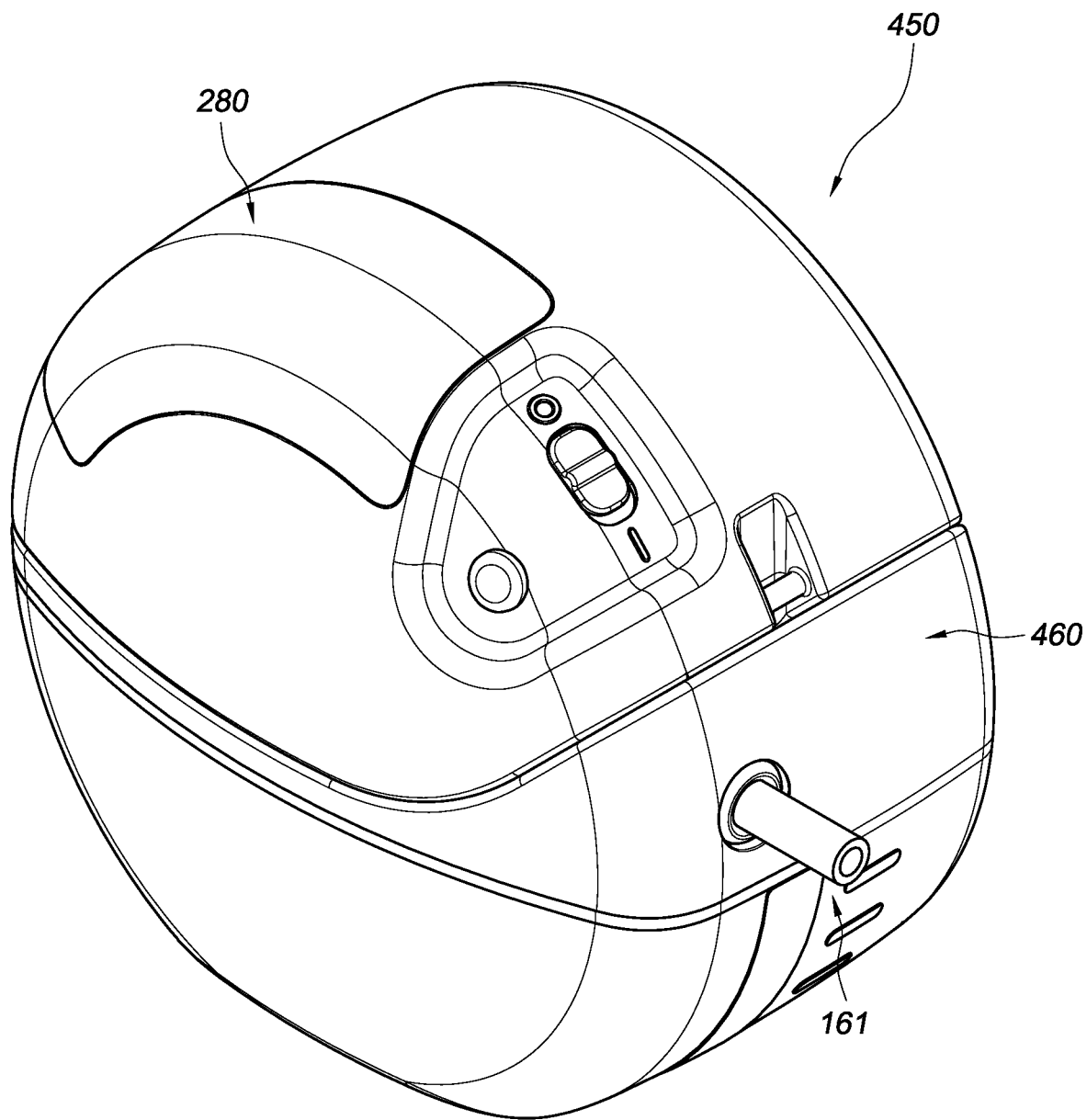
FIG. 4 shows in a perspective view an embodiment of the TNP system with a canister attached to the pump assembly.
Figure 5A:
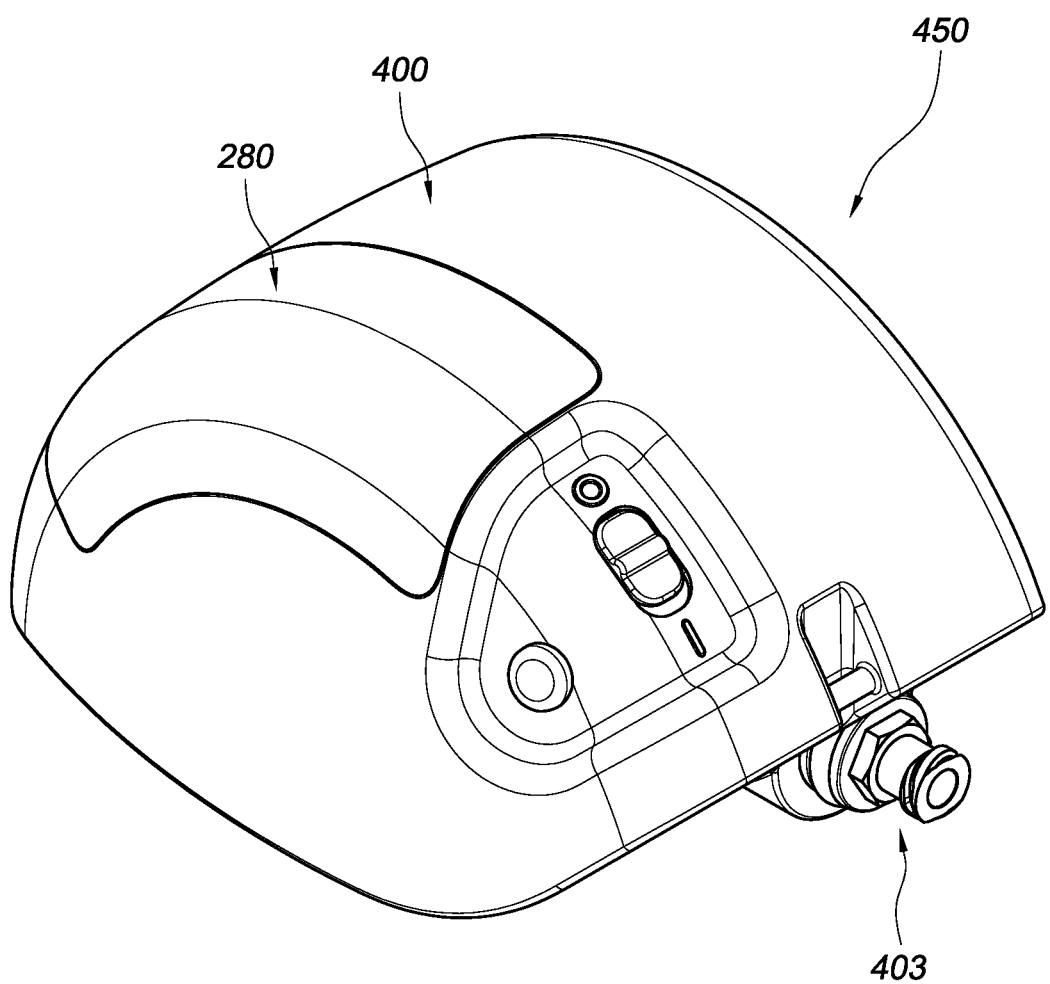
FIG. 5A shows in a perspective view an embodiment of the TNP system without a canister attached to the pump assembly according to some embodiments.
Figure 5B:
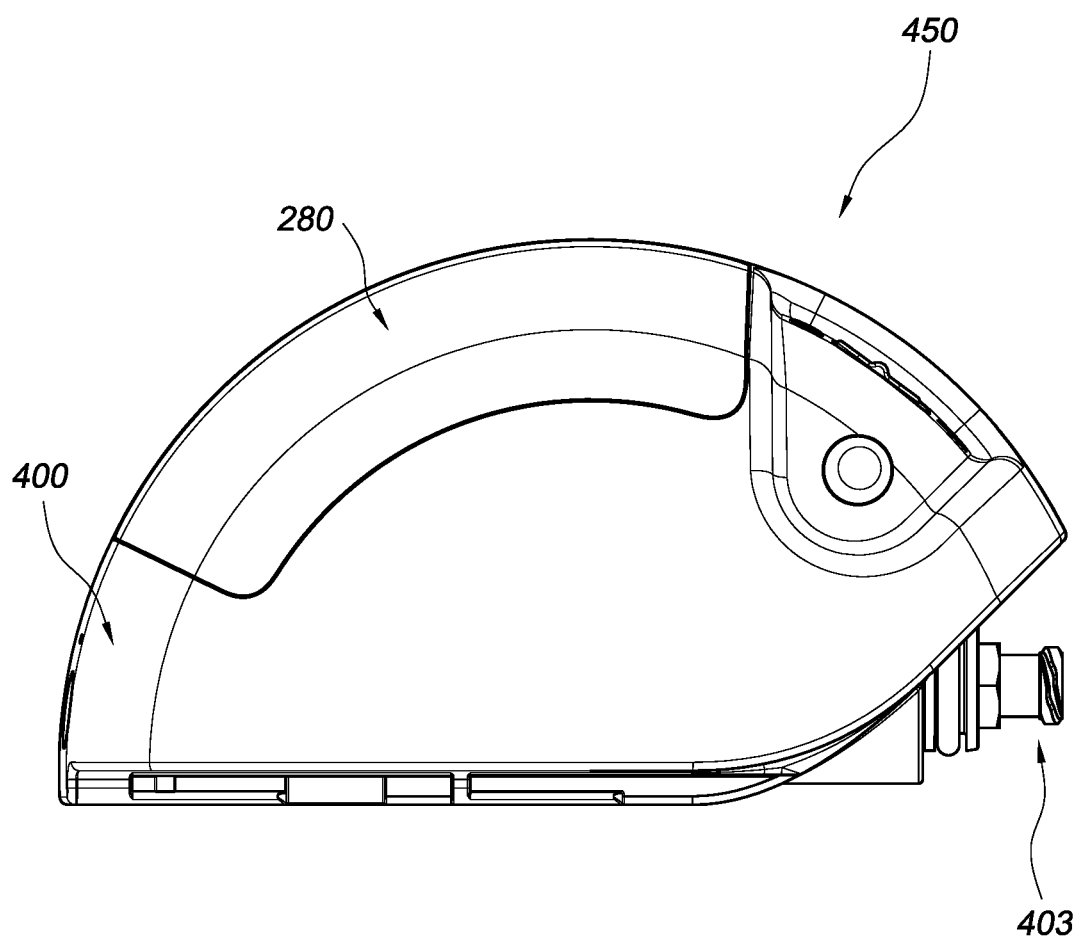
FIG. 5B shows a side view of the TNP system of FIG. 5A.
Figure 5C:
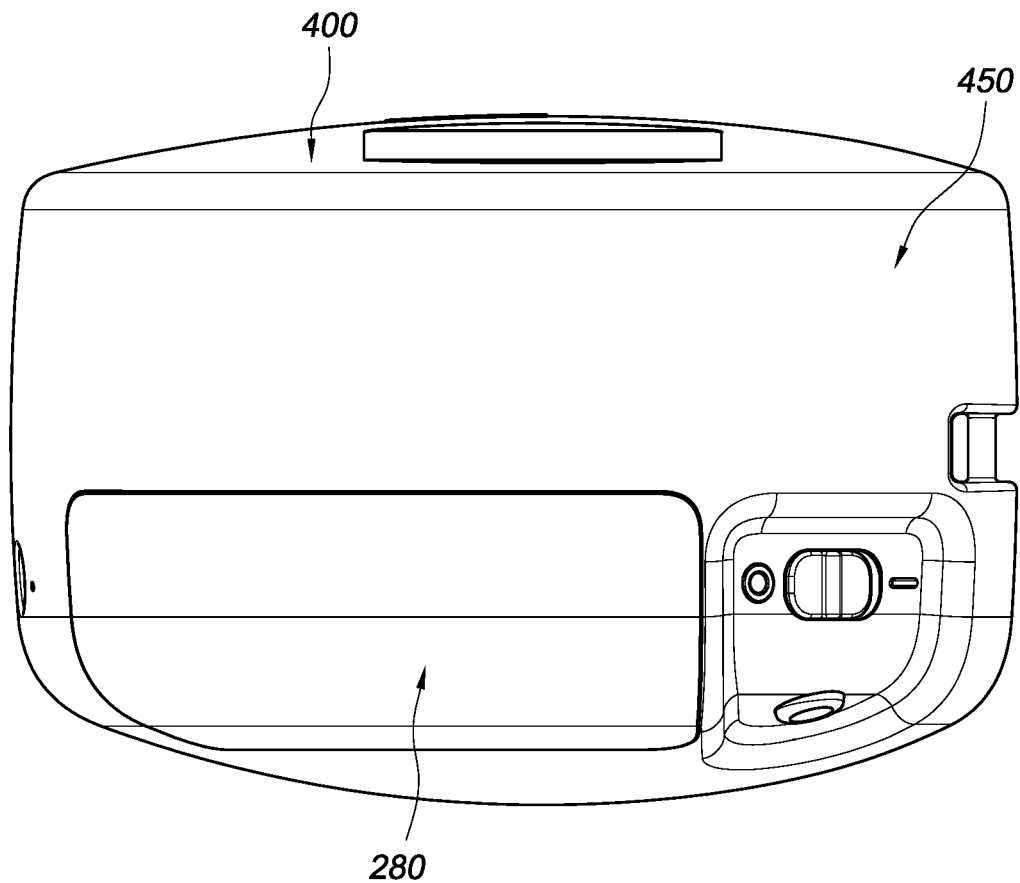
FIG. 5C shows a top view of the TNP system of FIG. 5A.
Figure 5D:
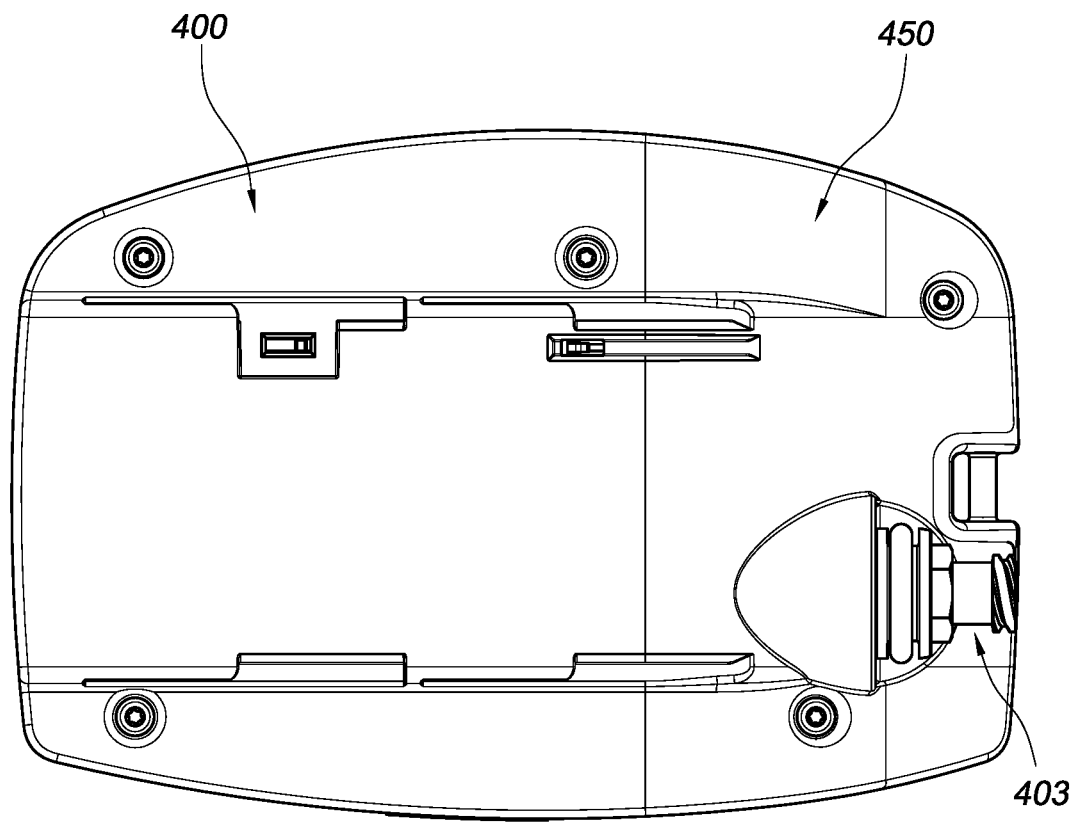
FIG. 5D shows a bottom view of the TNP system of FIG. 5A.
Figure 6A:
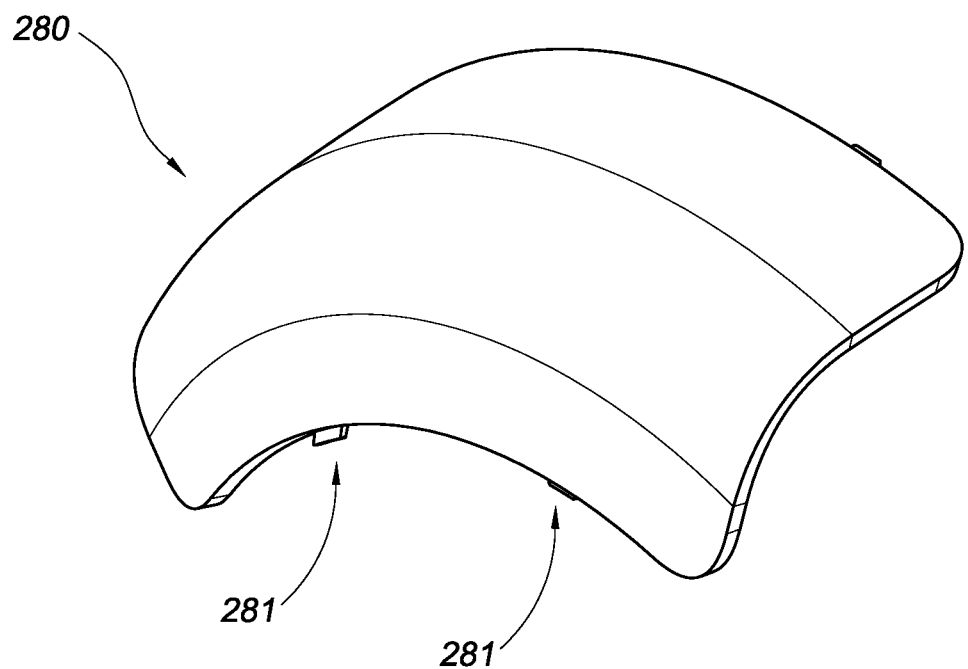
FIG. 6A shows in a perspective view an embodiment of a panel configured to be removably attached to a TNP system according to some embodiments.
Figure 6B:
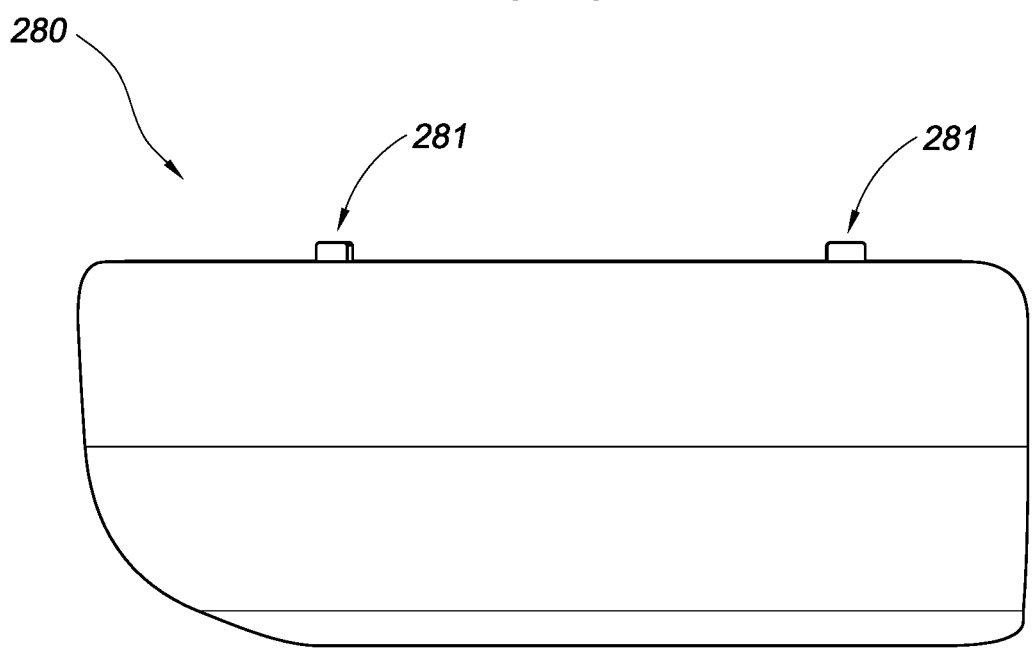
FIG. 6B shows a top view of the panel of FIG. 6A.
Figure 6C:
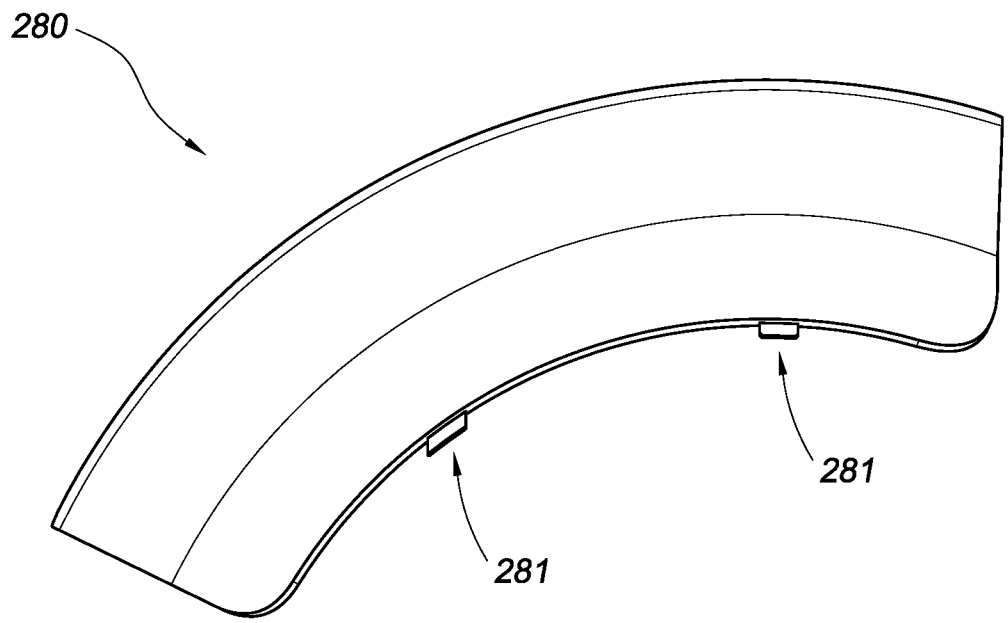
FIG. 6C shows a side view of the panel of FIG. 6A.
Figure 6D:
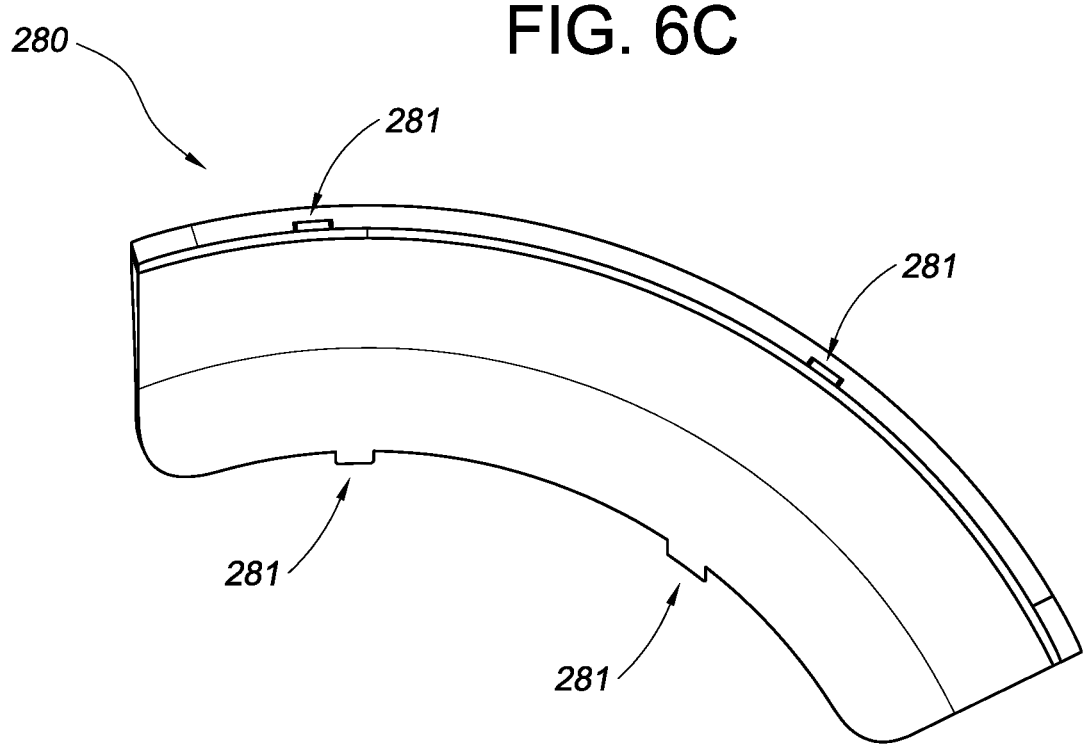
FIG. 6D shows another side view of the panel of FIG. 6A.
Figure 7A:
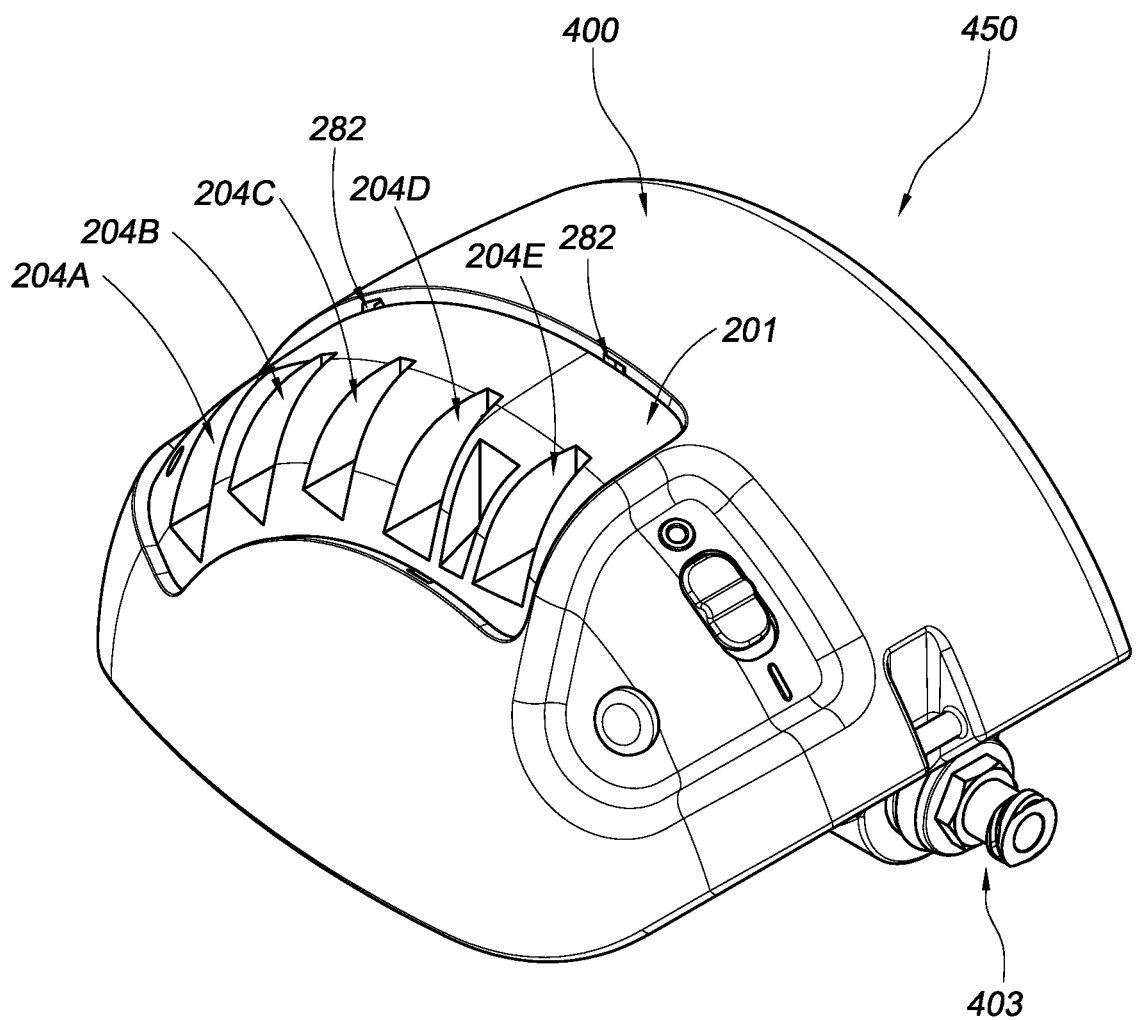
FIG. 7A shows in a perspective view an embodiment of the TNP system without a panel attached to the pump assembly according to some embodiments.
Figure 7B:
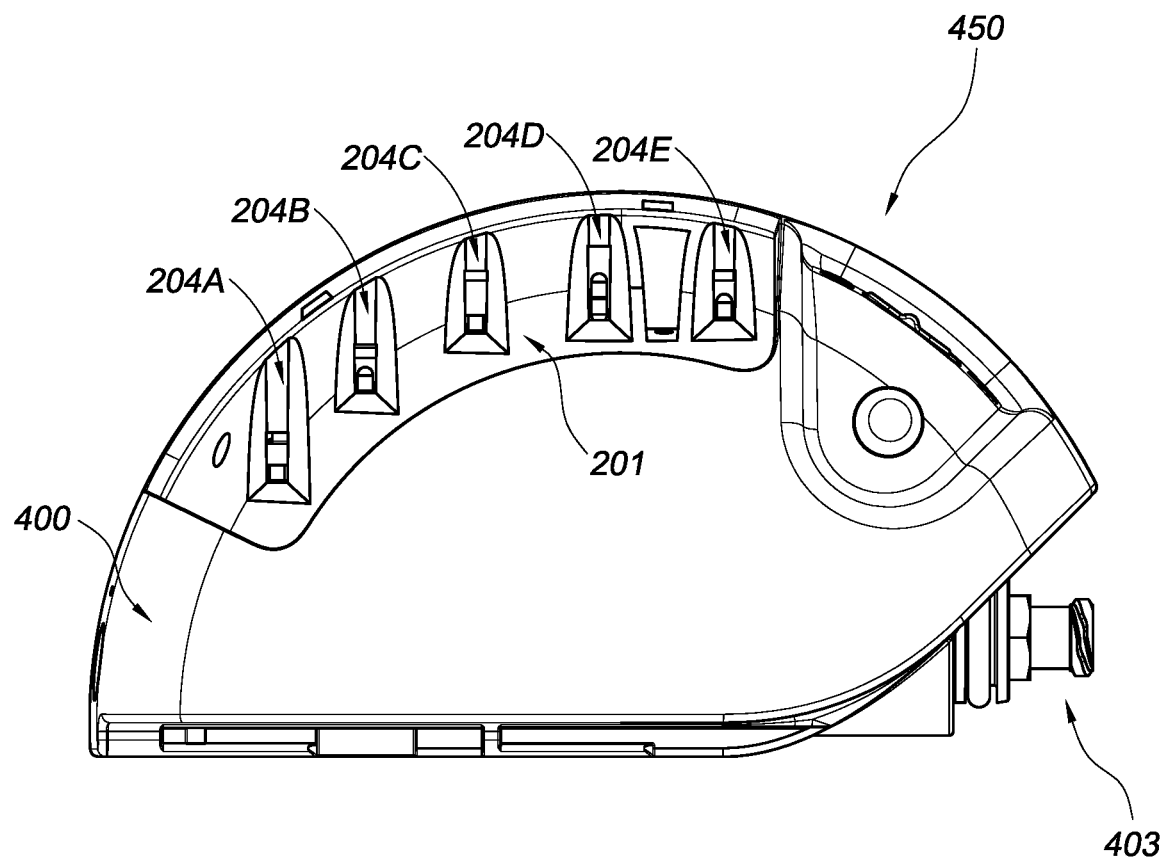
FIG. 7B shows a side view of the TNP system of FIG. 7A.
Figure 7C:
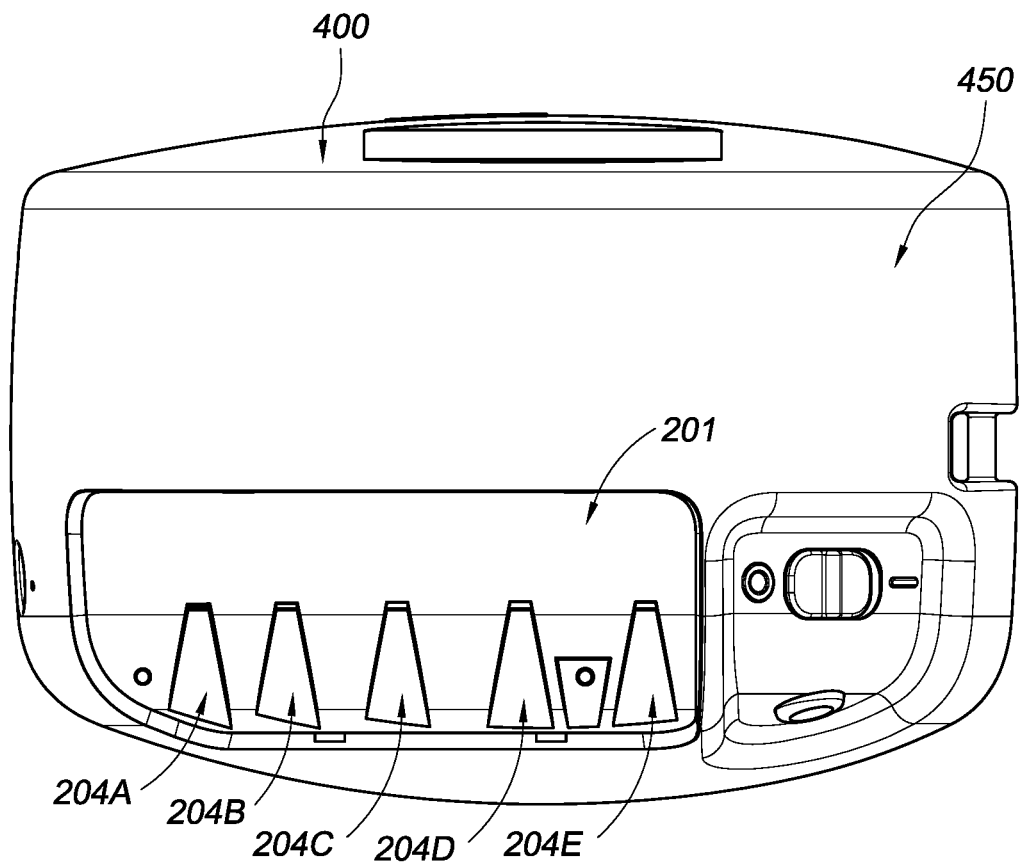
FIG. 7C shows a top view of the TNP system of FIG. 7A.

FIG. 4 depicts in a perspective view an embodiment of the TNP system according to some embodiments. In the illustrated system, a canister 460 is attached to the pump assembly 450. The canister 460 can have an inlet 161 through which wound exudate can enter the canister 460. In some embodiments, the pump assembly 450 may slide back to disengage the pump assembly 450 from the canister 460. The connector port 403 (shown in FIGS. 5A-5D and 7A-7C) of the pump assembly 450 can then be exposed when the canister 460 is disengaged from the pump assembly 450.

FIGS. 5A-5D depict in perspective, side, top, and bottom views, respectively, an embodiment of the TNP system according to some embodiments. In the illustrated system, a canister is not attached to a pump assembly, which can be the same as the pump assembly 450, thereby exposing the connector port 403, which can be the same as the connector port 203. As discussed herein, the pump assembly 450 may include one or more panels 280 removably attached to the housing, such as the housing 400. As described in further detail herein, the pump assembly 450 may include a switch configured to detect when and/or what type of panel, such as the panel 280, is attached to the pump assembly 450. In some embodiments, the panel 280 can align with one or more indicators 204 (shown in FIGS. 7A-7C and 8B) when the panel 280 is attached to the pump assembly 450, as described in further detail below.

FIGS. 6A-6D illustrate a panel, such as the panel 280, according to some embodiments. In the illustrated embodiment, the panel 280 has a semi-spherical profile configured to engage with a corresponding shape of the housing 400 of the pump assembly 450. However, it will be understood by one of ordinary skill in the art that the panel 280 and/or housing 400 may comprise any shape or size suitable for removable attachment of the panel 280 to the housing 400.

The housing 400 and/or panel 280 can include one or more attachment features that help secure the panel 280 to the pump assembly 150. For example, the housing 400 can have a recessed portion 201 along at least a portion of the housing 200. The recessed portion 201 (shown in FIGS. 7A-C and 8B) may be configured to retain one or more panels 208. Alternatively, the housing 400 may not include a recessed portion and the one or more panels 208 may be removably attached to an outer surface of the housing 400.

In some instances, a panel 208 may include one or more securement mechanisms, such as protrusions or tabs 281, as shown in FIGS. 6A-6D. The one or more securement tabs 281 can extend from one or more sidewalls of the panel 280. The securement tabs 281 may be adapted to be received into corresponding slots 282 (shown in FIGS. 7A-7C) on pump assembly 150. The slots 282 can be "L"-shaped to allow the tab 281 to be inserted into the slot 282 in a first direction and then slid in a second direction that is substantially perpendicular to the first direction to align the tab 281 with an overhang.

The attachment feature contemplated herein may comprise any additional structure configured to sufficiently permit the panel 280 to be removably attached to the housing 200. For example, the attachment feature can include a peg, a barb, a screw, or other protruding structure, configured to engage the housing 200 by a screw fit, snap fit, interference fit, or otherwise. In some embodiments, the attachment feature may include a protrusion extending radially outward from a sidewall of the panel 280. In some instances, the attachment feature may include an opening configured to receive a portion of the housing 400. The opening can include a circumferential groove that extends around the panel 280 to receive a corresponding protrusion of the housing 400.

In some embodiments, a pump assembly, such as the pump assembly 450 can be configured so that multiple panels 280 cannot be attached to the pump assembly 450 at the same time. For example, the housing 400 may engage with only a single panel 280. The attachment of a first panel 280A can block the attachment of any subsequent panel 280. Alternatively, the recessed portion 201 and/or a panel 280 may be adapted to permit the attachment of more than one panel 280 to the pump assembly 450. For example, the housing 400 may be sized and configured to receive two or more panels 280 within one or more recessed portions 201. In some instances, attachment of multiple panels 280 to the pump assembly 450 may cause the pump assembly 450 (for example control board 206) to adjust one or more operational parameters of the pump assembly 450.

With reference to FIGS. 3A and 7A-7C, one or more indicators 204 of the user interface can signal one or more operating or failure conditions of a pump assembly, such as the pump assembly 450, according to some embodiments. Each of the one or more indicators 204 may provide an indication regarding a different operating or failure condition. In some implementations, an active (for example, lit) indicator of the one or more indicators 204 can represent a certain operation condition for the pump assembly 450. For example, a dressing indicator of the one or more indicators 204 can provide an indication as to presence of leaks in the TNP system (such as, in the fluid flow path, which includes the dressing, pump assembly, and one or more lumens connecting the pump assembly to the dressing), and an active dressing indicator can represent a leak. As another example, a dressing capacity indicator of the one or more indicators 204 can provide an indication as to the remaining fluid capacity of the wound dressing or canister, and an active dressing capacity indicator can represent that the wound dressing or canister is at or nearing capacity. In some instances, a battery indicator of the one or more indicators 204 can provide an indication as to remaining capacity or life of a power source, such as batteries, and an active battery indicator can represent a low capacity. In some embodiments, the one or more indicators 204 can represent a combination of one or more of the above operating or failure conditions of the pump assembly 450 or other operating or failure conditions for the pump assembly 450.

As described herein, the pump assembly may include a user interface. The user interface can include a button that activates and deactivates therapy (such as a play/pause button) and one or more indicators. For example, the interface can include a low battery indicator, a full canister indicator, a leak indicator, and a blockage indicator. In some embodiments, the one or more panels 280 may be configured to form part of the user interface, such as one or more displays, indicators, lights, buttons, switches, speakers, vibrating elements, etc., as described herein. The user interface can be adjusted in response to the attachment of the one or more panels 280.

In some instances, the one or more panels 280 can be configured to interact with the indicators 204. For example, on a panel 280 signaling a canister mode, the user interface can include an indicator (for example an icon, audible alert, tactile response, etc.) alerting a user when canister becomes full. In canisterless mode, this indicator can be replaced with an indicator alerting the user when the dressing becomes full. In some embodiments, the panel 280 can comprise one or more icons configured to be activated by the one or more indicators 204. The one or more panels 280 may be removably attached to the housing 400 to cover the indicators 204, thereby permitting the indicators 204 to activate the one or more icons located on the panel 280.

Figure 8A:
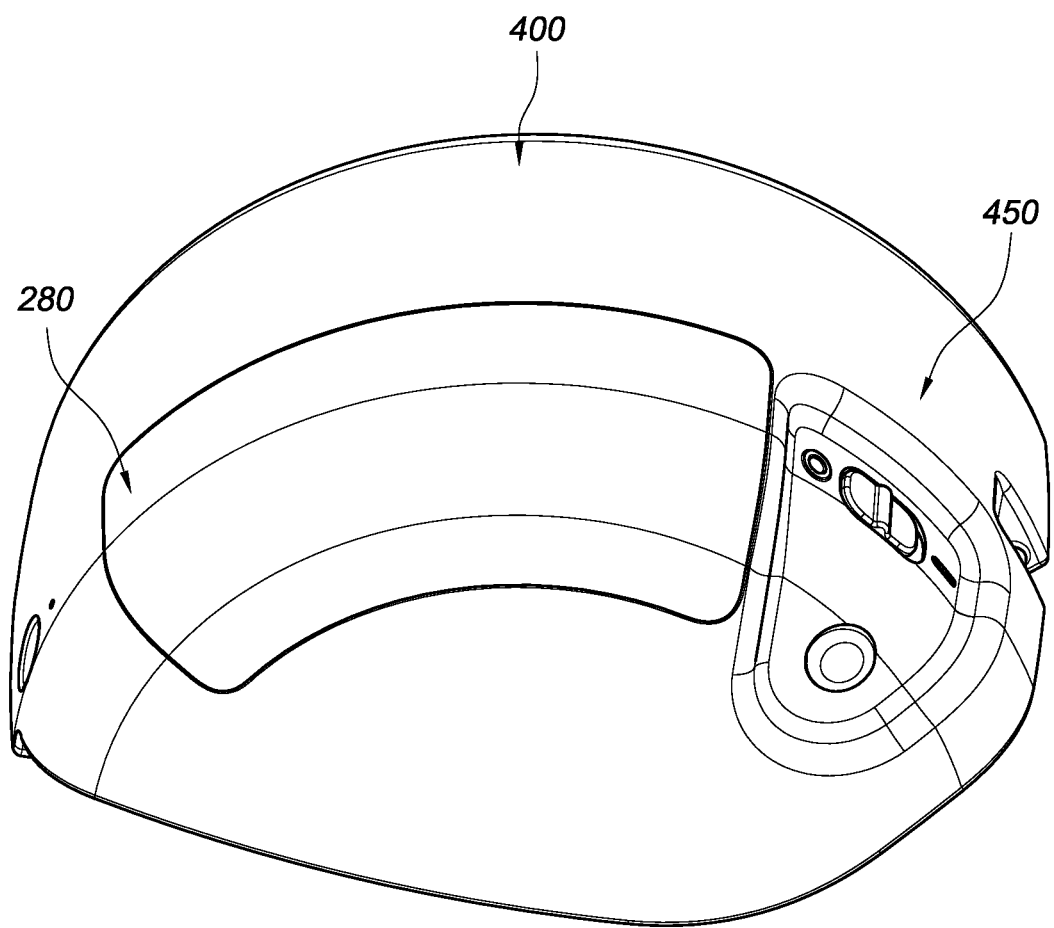
FIG. 8A shows in a perspective view another embodiment of the TNP system with a panel removably attached to the pump assembly according to some embodiments.
Figure 8B:
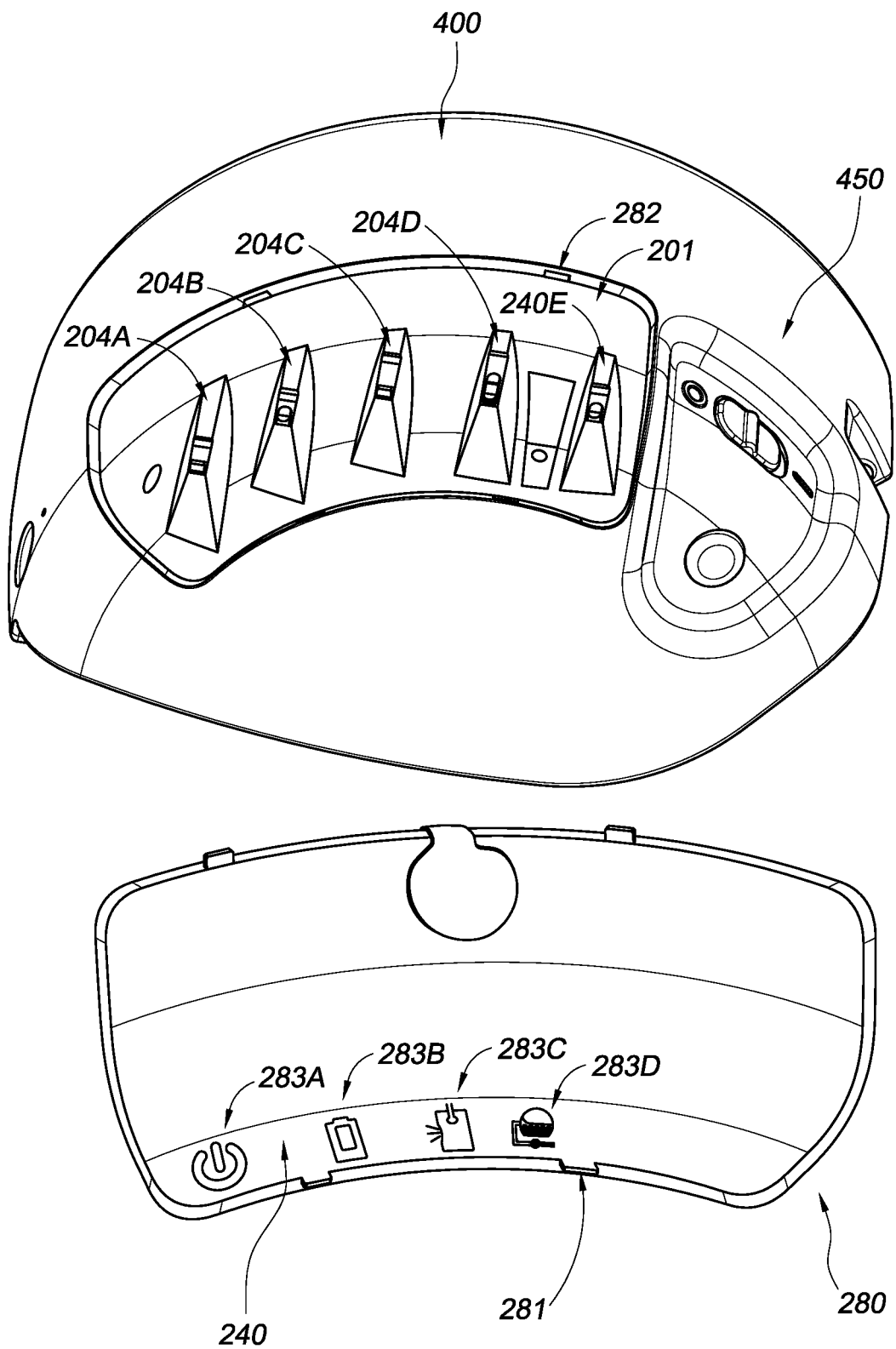
FIG. 8B shows a perspective view of the TNP system of FIG. 8A with the panel detached from the TNP system according to some embodiments.

With reference to FIGS. 8A-8B, the one or more indicators 204A-204E may comprise an illumination source, such as LEDs (not shown), configured to illuminate one or more icons 283A-283E of the panel 280. In some embodiments, the icons 283A-283E may form at least a portion of a user interface 240 of the panel 280. The one or more icons 283A-283E and/or indicators 204A-204E can, for instance, be of a different color, two different colors (for example, two indicators can share the same color), or same color. The indicators 204A-204E may be located within one or more apertures of a housing, such as the housing 400. The apertures may function to align the one or more icons 283A-283E of the panel with a respective indicator 204, thereby permitting the indicator 204 to selectively activate one or more icons 283A-283E of the panel 280.

The icons 283A-283E illustrated on a panel 280 may be varied. For example, a second panel 280B configured to indicate the presence of a canister may contain one or more icons 283A-283E not present and/or different than a first panel 280A configured to indicate the absence of a canister. In some instances, the attachment of a particular panel 280 to the pump assembly 150 may disable one or more of the indicators 204A-204E. For example, a full canister icon can be disabled and a full dressing indicator can be enabled due to the attachment of a canisterless panel 280A to the pump assembly 450. In some embodiments, an indicator for canister full and dressing full can share the same indicator (for example, light) and the indication changes depending on the panel 280 attached to the pump assembly 450 and a corresponding mode of operation (for example, light color changes to indicate canister full or dressing full).

In the embodiment illustrated in FIG. 8B, icon 283A can indicate if the pump assembly is turned on or off, icon 283B can indicate if the power source is becoming depleted or not, icon 283C can indicate if a leak is present or not, and icon 283D can indicate if the canister is full or not.

In some embodiments, one or more of the indicators 204 and/or the panel 280 can include visual, audible, tactile, and other types of indicators or alarms configured to signal to the user various operating conditions. Such conditions include system on/off, standby, pause, normal operation, dressing problem, leak, error, and the like. The pump assembly, such as the pump assembly 450, and/or the panel 280 can include speakers, displays, light sources, etc., or combinations thereof. In various implementations, a panel 280 may include one or more buttons on a touchscreen interface.

In some embodiments, a housing, such as the housing 400, can include one or more detectors or switches that are in electrical communication with a controller, such as the control board 206. The one or more switches can be configured to engage one or more panels, such as the panels 280. As described herein, the one or more panels 280 can signal the presence of a canister, or lack thereof, to indicate an operating mode of a pump assembly, such as the pump assembly 450. In some embodiments, the one or more switches can advantageously permit the pump assembly 450 (for example, the control board 206 shown in FIG. 3A) to differentiate between a canister connection and a dressing connection depending on the panel 280 attached to the housing 400. The switches contemplated herein can be mechanical, electrical, optical, and/or magnetic, proximity (such as, RFID), or any other suitable switch, and can include sensors and the like. For example, the switches may comprise one or more of a capacitive sensor, an inductive sensor, an infrared sensor, an ultrasonic sensor, a photodetector, or the like. The switches can be configured to close or open an electrical circuit, thereby permitting the control board 206 to detect whether and/or which type of panel 280 is engaged or disengaged. For example, as described in more detail below, the housing 400 can include a switch that is actuated by a portion of the panel 280 that couples to the housing 400. The switch can be further configured so that the switch is not actuated by a different panel 280 indicating a different mode of operation, thereby allowing the control board 206 to detect whether a canister or a dressing is attached to a pump assembly. In some arrangements, the pump assembly 450 can be configured so that the switch is activated by a panel 280 indicating that a dressing is coupled to the pump assembly and is not activated by a panel 280 indicating that a canister is coupled to the pump assembly 450.

The panel 280 can include one or more a securement tabs 281 that extends from the panel 280, as discussed herein with reference to FIGS. 6A-7C. The tab 281 can be arranged so that when the panel 280 is attached to the pump assembly 450, the tab 281 is received into the one or more slots 280 (shown in FIGS. 7A-7C) disposed on the housing. The slot 280 can include a switch that is actuated when the tab 281 is received into the slot 280. In this way, the switch can be actuated by the tab 281 when the pump assembly 450 is connected to a panel 280. In some instances, the location of the tabs 281 on the panel 280 may vary between a first panel 280A and a second panel 280B. The variation in the tab 281 location may cause the first panel 280A to activate one or more switches when attached to the housing that are not activated when the second panel 280B is attached to the housing. For example, the second panel 280B may signal the pump assembly 450 to operate in a canister mode based on the switches activated by the tabs 281 of the first panel 280A.

In some embodiments, a switch can have a first position corresponding to a first state of the switch (for example, unactuated) and a second position corresponding to a second state of the switch (for example, actuated). The pump assembly, such as the pump assembly 450, can detect the configuration of the switch and adjust one or more operational parameters of the pump assembly 450 based on the detected configuration of the switch. Such detection can be performed by, for example, the control board 206. In some arrangements, a second panel 280B indicating the canister mode deactivates the switch when the second panel 280B is attached to the pump assembly 450. In some arrangements, the second panel 280B activates the switch when the second panel 280B is attached to the pump assembly 450. In certain arrangements, the switch does not have an unactuated state but rather toggles from a canister position to a canisterless position based on whether the switch is contacted by at least a portion of the first panel 280A that is attached to the pump assembly 450.

In some implementations, the switch can be adapted to close an electrical circuit when the switch is actuated. The switch can be adapted so that the electrical circuit is open when the switch is not actuated. The switch can be adapted so that the switch is closed when a first panel 280A is attached to the housing and is open when a second panel 280B is attached to the housing. The control board 206 can be adapted to detect whether the electrical circuit is in the open or closed configuration. The control board 206 can be adapted to detect whether a first panel 280A indicating a canisterless mode or a second panel 280B indicating a canister made is attached to the housing.

The panel 280 may include one or more connectors that are configured to complete an electrical circuit of the pump assembly when the panel 280 is attached to the housing. For example, the connector can have a conductive material disposed on an inner surface of the panel 280. When the panel 280 is attached to the housing, and the corresponding one or more switches, the conductive ring of material disposed on the inner surface of the panel 280 can establish an electrical connection of the electrical circuit. The control board 206 of the pump assembly can be configured to detect when an electrical connection is made, thereby signaling to the pump assembly that the pump assembly should operate in a canister mode or a canisterless mode.

In some implementations, the switch can include a magnetic proximity sensor (for example, Hall effect sensor, RFID, or the like) to detect when and/or which type of panel 280 is attached to the pump assembly. A panel 280 can have a magnet embedded into the panel 280. When the panel 280 is attached to the housing, the magnet embedded in the panel 280 will be brought close to the magnetic proximity sensor of the pump assembly. The magnetic proximity sensor can detect the presence of the magnetic field of the panel magnet. Accordingly, the magnetic proximity sensor can activate a detector circuit on the pump assembly to indicate that the pump assembly operates in either a canister mode or a canisterless mode.

As described above, these various implementations advantageously allow the pump assembly to differentiate between different types of panels 280, such as, for example, between canister-signaling panel 280B and canisterless-signaling panel 280A. The pump assembly can, for example, thereby automatically determine whether to function in one or more different modes of operation, such as a canister-connected mode or canisterless mode. The one or more different modes of operation can differ, for instance, at least in the associated pump operating pressure settings like pressure thresholds, rates of change, or timings of pressure changes.

In some embodiments, one or more switches configured to interact with a panel 280 can be disposed within the recessed portion 201 of the housing. For example, a recessed portion 201 can have a pair of switches disposed across from one another on the recessed portion 201 of the housing. However, the housing need not have two switches. For example, the housing can have one, three, or more than three switches. In embodiments that have multiple switches, the switches can be spaced apart circumferentially from an adjacent switch by more or less than 180 degrees. In some embodiments the one or more switches can be disposed on a side of the housing.

In some instances, the pump assembly can include one or more switches in addition to or in lieu of the switch configured to engage the one or more panels 280. The one or more additional switches can be adapted to be actuated when a canister connector is connected to the pump assembly. In some arrangements, the pump assembly can include one or more additional switches that are actuated when a canisterless connector is connected to the pump assembly. In certain arrangements, the pump assembly can include at least one additional switch that is actuated when the connector port is connected to one but not to the other of a canister connector and a cansisterless connector. In some arrangements, the at least one additional switch can be disposed at the connector port.

As described herein, the pump assembly is configured to operate in one or more operating modes. The TNP system can activate the negative pressure source to provide or achieve a particular set point or target level of negative pressure at the wound (for example, under the wound dressing). As the TNP system can be configured to operate with a canister or without the canister, provision of negative pressure wound therapy can be performed according to canister and canisterless modes, in which one or more operating parameters may be different. In some embodiments, the target level of negative pressure provided by the negative pressure source to the wound can be adjustable or selectable when the TNP system operates in canister mode. In canisterless mode, the target level of negative pressure may be set to a particular value and may not be adjustable.

In some implementations, a controller can operate the negative pressure source differently depending on canister or canisterless mode of operation. For example, in canister mode of operation, the negative pressure source can be operated continuously based on feedback from a pressure sensor that measures pressure in the fluid flow path (which can directly or indirectly indicate pressure at the wound). The controller may alter the negative pressure source in response to detection that a panel, such as the panel 280, is attached to a housing.

In certain implementations, canisterless mode of operation can involve controlling the negative pressure source to be activated while the target level of negative pressure is being established at the wound and, subsequently, be deactivated. When, due to one or more leaks, negative pressure at the wound falls below the target level of negative pressure (for example, below an threshold level in relation to the target level of negative pressure), the negative pressure source can be re-activated to re-establish the target level of negative pressure at the wound. In canisterless mode, the negative pressure source may not be operated continuously.

In some embodiments, the TNP system can provide one or more indications associated with changing the operating mode of the pump assembly. As disclosed herein, the one or more indications can be visual, audible, tactile, and the like. In some cases, indication can alternatively or additionally involve deactivating the source of negative pressure. For example, the negative pressure source can be deactivated when at least one of a blockage or leakage has been detected.

Figure 9:
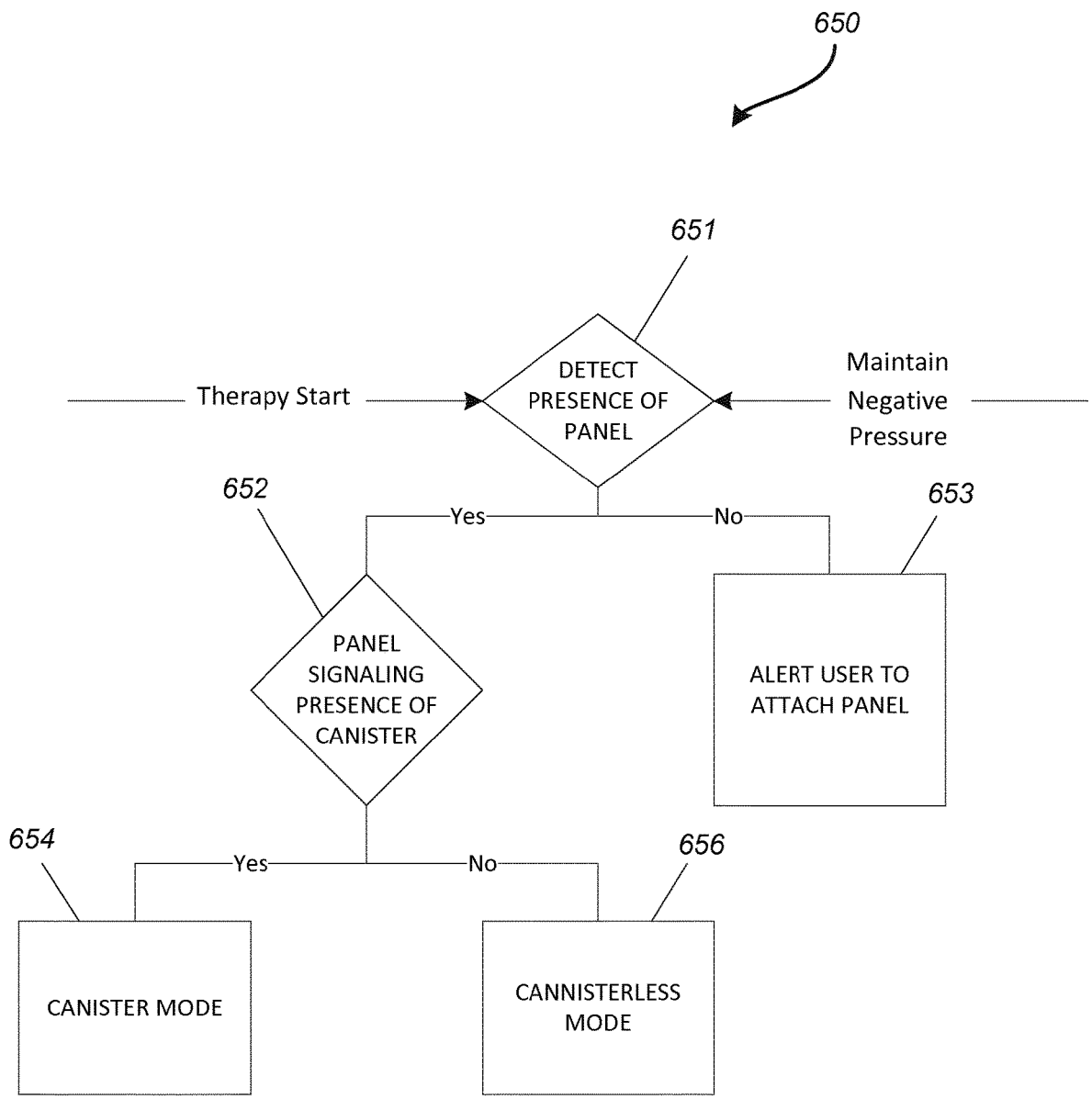
FIG. 9 illustrates a process of operation of a TNP system according to some embodiments.

FIG. 9 illustrates a process 650 of operation of a TNP system according to some embodiments. The process 650 can be implemented by a controller, such as the control board 206. The process 650 starts in state 651 in which the process 650 detects whether a panel is attached to a housing. Detection can be performed using any of the approaches and switches described herein. State 651 can be executed when therapy is started or after when the target level of negative pressure at the wound is being maintained.

In state 651, if presence of a panel is detected, the process transitions to state 652. If one or more panels 280 are not detected, the process may proceed to state 653. In state 653, the process 650 may alert a user to attach a panel 280 to the housing. The alert within state 653 may be performed via one or more user interface modalities described herein.

At state 652, the process 650 detects whether the attached panel indicates the presence of a canister in the fluid flow path. In some embodiments, the TNP system can be switched from canister to canisterless mode or vice versa while negative pressure therapy is being provided (for example, while the negative pressure source is active) without interrupting therapy. For instance, while negative pressure therapy is being provided, a first panel can be removed and/or a second panel can be attached, and the TNP system can be configured to detect this change without deactivating the negative pressure source. In certain implementations, negative pressure wound therapy can be interrupted when the TNP system is switched from canister to canisterless mode or vice versa.

In state 652, if the process 650 determines that the attached panel indicates the presence of a canister, the process transitions to state 654 in which the TNP system operates in the canister mode as described herein. If the attached panel does not indicate the presence of a canister, the process 650 transitions to state 656 in which the TNP system operates in the canisterless mode as described herein.

Other Variations

Although this disclosure describes certain embodiments, it will be understood by those skilled in the art that many aspects of the methods and devices shown and described in the present disclosure may be differently combined and/or modified to form still further embodiments or acceptable examples. All such modifications and variations are intended to be included herein within the scope of this disclosure. Indeed, a wide variety of designs and approaches are possible and are within the scope of this disclosure. No feature, structure, or step disclosed herein is essential or indispensable. Moreover, while illustrative embodiments have been described herein, the scope of any and all embodiments having equivalent elements, modifications, omissions, combinations (for example, of aspects across various embodiments), substitutions, adaptations and/or alterations as would be appreciated by those in the art based on the present disclosure. While certain embodiments have been described, these embodiments have been presented by way of example only, and are not intended to limit the scope of protection.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially"

as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, 0.1 degree, or otherwise.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A negative pressure apparatus comprising:
   a pump housing comprising a pump, a controller, and at least one light source; and
   a panel removably attachable to the pump housing and configured to cover the at least one light source, the removable panel comprising one or more icons,
   wherein the at least one light source is configured to illuminate the one or more icons when the removable panel is attached to the pump housing, and
   wherein the controller is programed to:
      determine a type of the removable panel attached to the pump unit, and
      change one or more pump settings based on the determination.

2. The negative pressure apparatus of claim 1, wherein the at least one light source is configured to illuminate the one or more icons in response to detection, by the controller, of at least one of a plurality of conditions.

3. The negative pressure apparatus of claim 2, wherein the plurality of conditions comprises at least one of a power on, low battery, leak, or canister full.

4. The negative pressure apparatus of claim 1, wherein the pump housing is configured to permit attachments of a plurality of removable panels each including a different arrangement of icons.

5. A negative pressure apparatus comprising:
   a pump housing comprising a pump configured to provide, via a fluid flow path, negative pressure to a wound configured to be covered by a wound dressing, the pump housing further comprising a controller; and
   one or more panels configured to be removably attachable to the pump housing and configured to indicate an operating mode,
   wherein the controller is programed to operate the pump in a first operating mode in response to a detection that a first panel is attached to the pump housing, the first operating mode associated with the first panel, and
   wherein the controller is further configured to adjust one or more operational parameters of the pump based on the first operating mode.

6. The negative pressure apparatus of claim 5, wherein the one or more operating modes comprises at least one of a canister mode or a canisterless mode.

7. The negative pressure apparatus of claim 5, wherein the pump housing further comprises a recess configured to receive the one or more panels.

8. The negative pressure apparatus of claim 5, wherein the pump housing further comprises a detector in communication with the controller, wherein at least some of the one or more panels are configured to engage the detector, the detector configured to indicate to the controller whether a canister is positioned in the fluid flow path between the pump and the wound based on output of the detector.

9. The negative pressure apparatus of claim 8, wherein:
   the first panel of the one or more panels is configured to indicate that the canister is positioned in the fluid flow path and is further configured to engage the detector when attached to the housing; and
   a second panel of the one or more panels is configured to indicate that the canister is not positioned in the fluid flow path and is further configured not to engage the detector when attached to the housing.

10. The negative pressure apparatus of claim 8, wherein the detector comprises at least one of a capacitive sensor, an inductive sensor, an infrared sensor, an ultrasonic sensor, an optical sensor, a photodetector, or mechanical switch.

11. The negative pressure apparatus of claim 5, wherein the one or more panels each comprises a plurality of icons.

12. The negative pressure apparatus of claim 11, wherein the pump housing further comprises plurality of light sources configured to illuminate one or more of the plurality of icons.

13. The negative pressure apparatus of claim 12, wherein the plurality of light sources is configured to illuminate one or more of the plurality of icons in response to the operating mode indicated by the first panel.

14. The negative pressure apparatus of claim 5, wherein the controller is further configured to:
   operate the pump in a second operating mode different from the first operating mode in response to a detection that a second panel is attached to the pump housing, the second operating mode being associated with the second panel, and
   adjust the one or more operational parameters of the pump based on the second operating mode.

15. A method of operating a negative pressure wound therapy apparatus, the method comprising:
   determining an operating parameter associated with a panel in response to the panel being removably connected to a housing comprising a negative pressure source;
   based on the operating parameter, determining that a canister or a wound dressing without a separate canister is fluidicially connected to the negative pressure source; and
   adjusting provision of negative pressure from the negative pressure source based on the determination;
   wherein the method is performed under control of a controller.

16. The method of claim 15, further comprising determining which panel of a plurality of panels is removably connected to the housing, each panel of the plurality of panels associated with a different operating parameter.

17. The method of claim 16, further comprising operating the negative pressure source in one or more modes in response to determining which panel is attached to the housing.

18. The method of claim 17, wherein operating in the one or more modes comprises adjusting one or more operational parameters of the negative pressure source based on the mode.

19. The method of claim 15, further comprising adjusting a user interface configured to provide at least one operational parameter of the apparatus based on the determination.

20. The method of claim 1, wherein the pump housing encases the pump, the controller, and the at least one light source when the removable panel is detached from the pump housing.

* * * * *